(12) United States Patent
Woloschuk et al.

(10) Patent No.: US 10,463,291 B2
(45) Date of Patent: Nov. 5, 2019

(54) RETRACTABLE BLOOD COLLECTION DEVICES AND METHODS

(71) Applicant: L.O.M. Laboratories Inc., Vancouver (CA)

(72) Inventors: Ralph E. Woloschuk, St. Albert (CA); Scott E. Castanon, Carlsbad, CA (US); Warren Marc Terry, Poway, CA (US); Joseph James Baker, Fallbrook, CA (US)

(73) Assignee: L.O.M. Laboratories Inc., Vancouver (CA)

( * ) Notice: Subject to any disclaimer, the term of this patent is extended or adjusted under 35 U.S.C. 154(b) by 219 days.

(21) Appl. No.: 15/559,745

(22) PCT Filed: Mar. 18, 2016

(86) PCT No.: PCT/CA2016/050313
§ 371 (c)(1),
(2) Date: Sep. 19, 2017

(87) PCT Pub. No.: WO2016/149810
PCT Pub. Date: Sep. 29, 2016

(65) Prior Publication Data
US 2018/0042539 A1  Feb. 15, 2018

Related U.S. Application Data

(60) Provisional application No. 62/136,067, filed on Mar. 20, 2015.

(51) Int. Cl.
*A61B 5/15* (2006.01)
*A61B 5/153* (2006.01)

(52) U.S. Cl.
CPC ........ *A61B 5/150572* (2013.01); *A61B 5/153* (2013.01); *A61B 5/15003* (2013.01); *A61B 5/150236* (2013.01); *A61B 5/150259* (2013.01); *A61B 5/150343* (2013.01); *A61B 5/150389* (2013.01); *A61B 5/150473* (2013.01); *A61B 5/150595* (2013.01); *A61B 5/150709* (2013.01);
(Continued)

(58) Field of Classification Search
CPC ........ A61B 5/150572; A61B 5/150236; A61B 5/150343; A61B 5/150595; A61B 5/150732; A61B 5/150885; A61B 5/153; A61B 5/154; A61B 2560/028; A61B 2560/0285; A61M 5/3232; A61M 5/3234; A61M 5/3241
See application file for complete search history.

(56) References Cited

U.S. PATENT DOCUMENTS

2002/0177819 A1* 11/2002 Barker ................ A61M 5/3234
604/232
2005/0261638 A1* 11/2005 Wright ................ A61M 5/3202
604/272

FOREIGN PATENT DOCUMENTS

| CA | 2835950 A1 | 12/2012 |
|----|------------|---------|
| CA | 2923448 A1 | 3/2015 |
| WO | 9824493 | 6/1998 |

(Continued)

*Primary Examiner* — Eric F Winakur
(74) *Attorney, Agent, or Firm* — Oyen Wiggs Green & Mutala LLP

(57) ABSTRACT

Blood collection devices having a retractable needle are provided. Activation of the retraction mechanism causes release of propellant from a propellant chamber, which drives a retraction assembly carrying the needle into a body of the device.

20 Claims, 27 Drawing Sheets

(52) U.S. Cl.
CPC .. *A61B 5/150717* (2013.01); *A61B 5/150732* (2013.01)

(56) References Cited

FOREIGN PATENT DOCUMENTS

| WO | 9844971 | | 10/1998 |
|---|---|---|---|
| WO | 2006024172 | A1 | 3/2006 |
| WO | 2006111731 | A2 | 10/2006 |
| WO | 2015145207 | A1 | 10/2015 |
| WO | 2016065484 | A1 | 5/2016 |
| WO | 2016115628 | A1 | 7/2016 |

\* cited by examiner

RETRACTABLE BLOOD COLLECTION DEVICES AND METHODS

CROSS-REFERENCE TO RELATED APPLICATIONS

This application is a 371 national phase entry of Patent Cooperation Treaty patent application No. PCT/CA2016/050313, which claims priority to, and the benefit of, U.S. provisional patent application No. 62/136,067 filed 20 Mar. 2015. Both of these applications are incorporated by reference herein in their entirety.

TECHNICAL FIELD

Some embodiments of the present invention pertain to blood collection devices having a retractable sharps element. Some embodiments of the present invention pertain to blood collection devices for use with conventional blood collection vials, the device having a retractable sharps element.

BACKGROUND

It is well known that many dangerous communicable diseases are spread through contacting the body fluids of an infected person. Needlestick injuries are accordingly of considerable concern to those involved in the treatment and care of people who may be infected with such diseases. Such diseases, which are in some cases life threatening, and in many cases expensive to treat, can be spread to healthcare personnel through accidental injuries occurring in the course of handling contaminated sharps.

Blood must be collected from individuals for many reasons, for example for diagnosis or monitoring of a medical condition, administration of certain drugs, or removal of blood for a specific reason. A significant number of needlestick injuries occur during the handling of blood collection devices. Some of these injuries may occur during use of the blood collection device, and some may occur after the device has been used but before the needle of the device has been rendered innocuous, for example by capping the needle.

Thus, there is a desire to provide blood collection devices that can minimize a risk of needlestick injury occurring. Retracting a needle of the blood collection device inside the device after use is one way to minimize the risk of a needlestick injury occurring.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides a blood collection device for use with a blood collection vial, the blood collection device comprising a housing having a proximal end configured to receive the blood collection vial, a needle retraction assembly positioned near a distal end of the housing and moveable between an initial assembled configuration and an activated configuration in response to the application of an activation force against the blood collection vial by a user, the needle retraction assembly having a spike plate having rupturing members extending distally of the needle retraction assembly and a needle hub engaged with other components of the needle retraction assembly in a first position where the needle retraction assembly is in the initial assembled configuration, and moveable to a second, sealed, position within the needle retraction assembly in response to the application of the activation force to move the needle retraction assembly to the activated configuration. A needle is supported by the needle hub, the needle having a distal end for piercing the skin of a subject and a proximal end for insertion through a cover of the blood collection vial. A propellant chamber is located distally of the spike plate, the propellant chamber having a seal for initially containing propellant, the seal being rupturable upon movement of the spike plate to the activated position to release the propellant, so that release of the propellant moves the needle retraction assembly and the needle in the proximal direction to retract the needle inside the housing.

Another aspect of the invention provides a blood collection device having a housing, a plunger slideably mounted within the housing, sidewalls of the plunger defining a retraction lumen within the plunger. A needle seal is frictionally engaged with the retraction lumen at a distal end of the plunger, the needle seal having a sealing engagement structure on a distal side thereof. A needle is initially secured at a distal portion of the housing, and a needle support structure is frictionally engaged in the distal portion of the housing for initially securing the needle in place, a first portion of the needle support structure being moveable in a distal direction in response to application of an activation force against the plunger by a user, a second portion of the needle support structure being shaped and configured to engage with the sealing engagement structure of the needle seal upon the application of the activation force against the plunger by the user to provide a needle retraction assembly including the needle. A propellant chamber is positioned in the housing distally of the needle support structure. Rupturing spikes are provided proximally of the propellant chamber and distally of the needle support structure, the rupturing spikes being moveable to rupture the propellant chamber upon the application of the activation force against the plunger by the user. A blood collection outlet is provided for passing blood flowing through the needle to a blood collection reservoir, and a blood flow path is provided through the needle and past the plunger to the blood collection outlet when the blood collection device is in its initial configuration. The application of the activation force against the plunger by the user moves the plunger distally within the housing to engage the needle seal with the second portion of the needle support structure to form the needle retraction assembly, and causes the first portion of the needle support structure to move distally within the housing to cause the rupturing spikes to release propellant from the propellant chamber, so that the released propellant retracts the needle retraction assembly and the needle within the retraction lumen.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

As used herein, the term "distal" means in a direction away from a user's hand, having regard to the orientation in which the blood collection device is intended to be used. The term "proximal" means the opposite of distal, i.e. in a direction toward a user's hand.

The term "outwardly" means in a radial direction away from the axial centerline of the blood collection device. The term "inwardly" means the opposite of outwardly, i.e. in a radial direction towards the axial centerline of the blood collection device.

The term "seals" or "sealingly engages" means that two components are engaged with sufficient sealing capability that the function for which the sealing is provided can be effectively performed.

Figure 1:
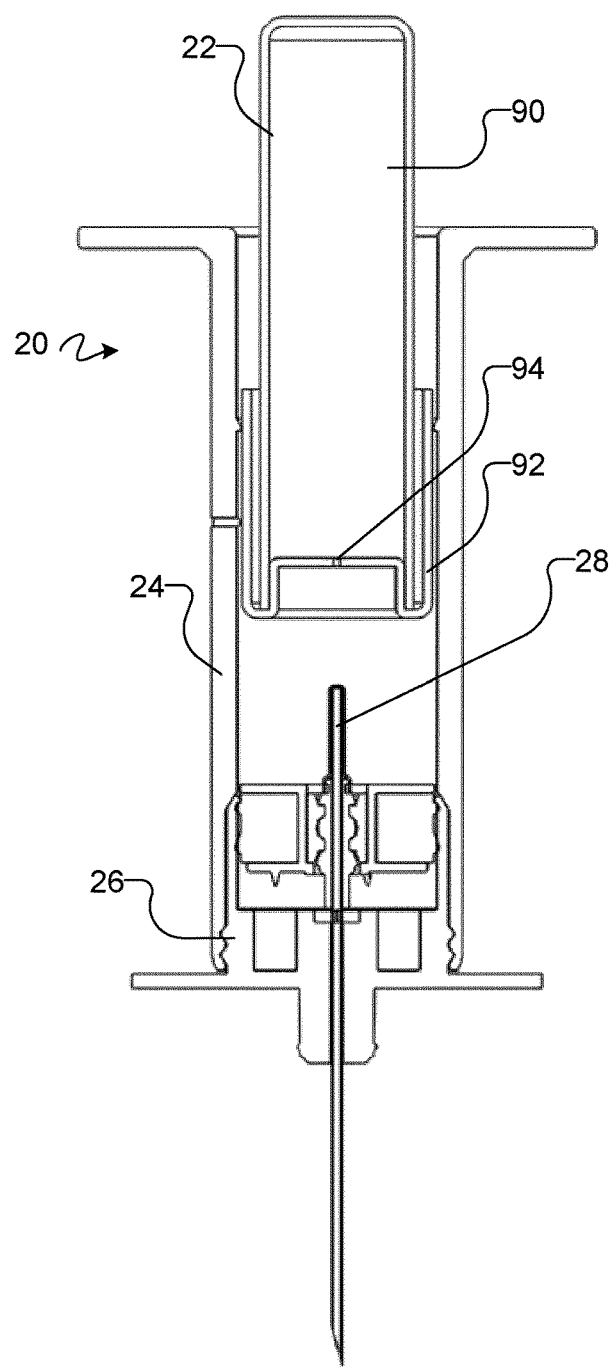
FIG. 1 is a cross-sectional view of an example embodiment of a retractable blood collection device, with a conventional blood collection vial partially inserted thereon.

With reference to FIG. 1, an example embodiment of a retractable blood collection device 20 that can be used with a conventional blood collection vial 22 (for example, a Vacutainer™ blood collection vial that is provided with a slight vacuum to assist in drawing blood into the vial) is illustrated. Blood collection device 20 has a main body 24 that is engageable with a needle assembly 26 that supports a cannula or needle 28. In some embodiments, main body 24 and needle assembly 26 could be provided as a single housing, rather than as two separate components.

In some embodiments, needle 28 is a double-ended needle, i.e. having two sharp ends, to facilitate both piercing the skin of a subject with the distal end of needle 28, and piercing a cap of blood collection vial 22 as described below. In the illustrated embodiment, only the distal end of needle 28 is sharp, and the proximal end of needle 28 is configured to be engaged by a small aperture 94 provided on the blood collection vial 22, and to be covered by a moveable sheath to regulate the flow of blood through needle 28 as described below. In some embodiments, the distal end of needle 28 is provided with a low angle bevel on its distal edge, to aid insertion of needle 28 into a vein.

Figure 2:
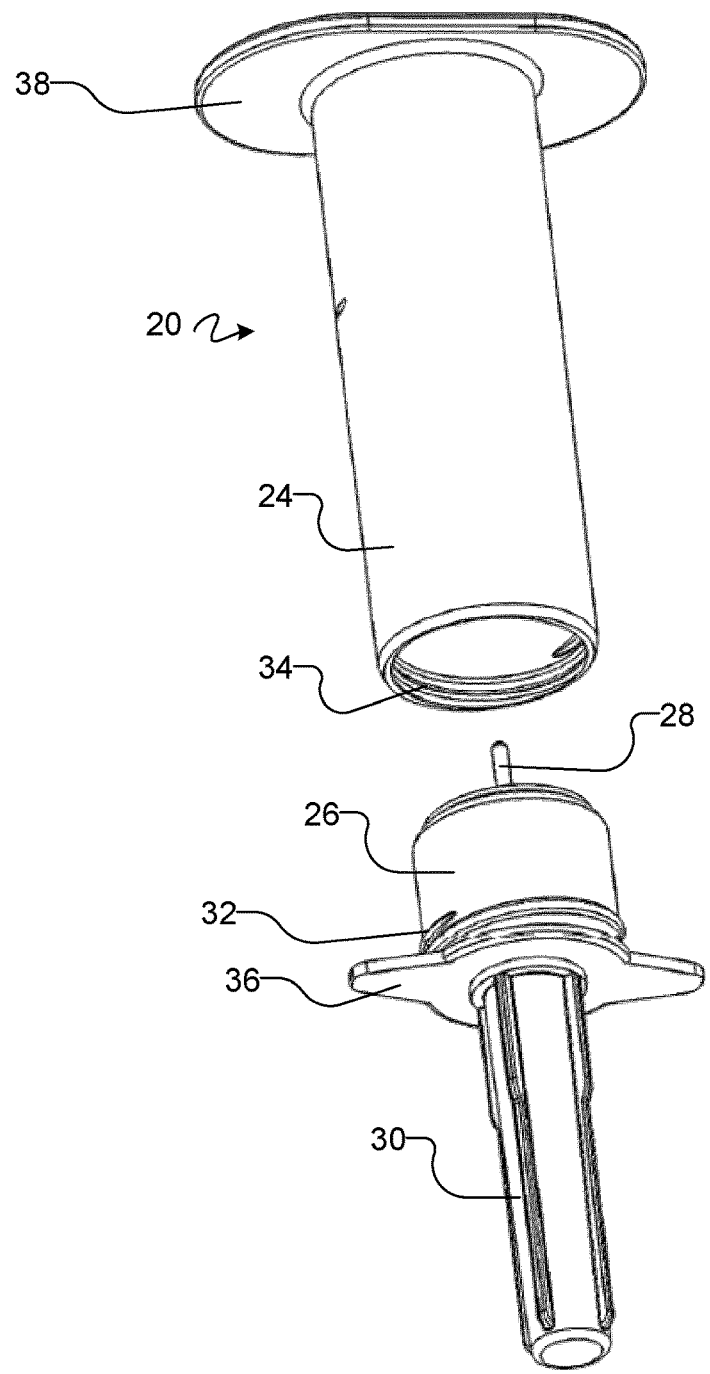
FIG. 2 is a perspective view of an example embodiment of a retractable blood collection device, with the needle assembly separated from the main body of the device.
Figure 3:
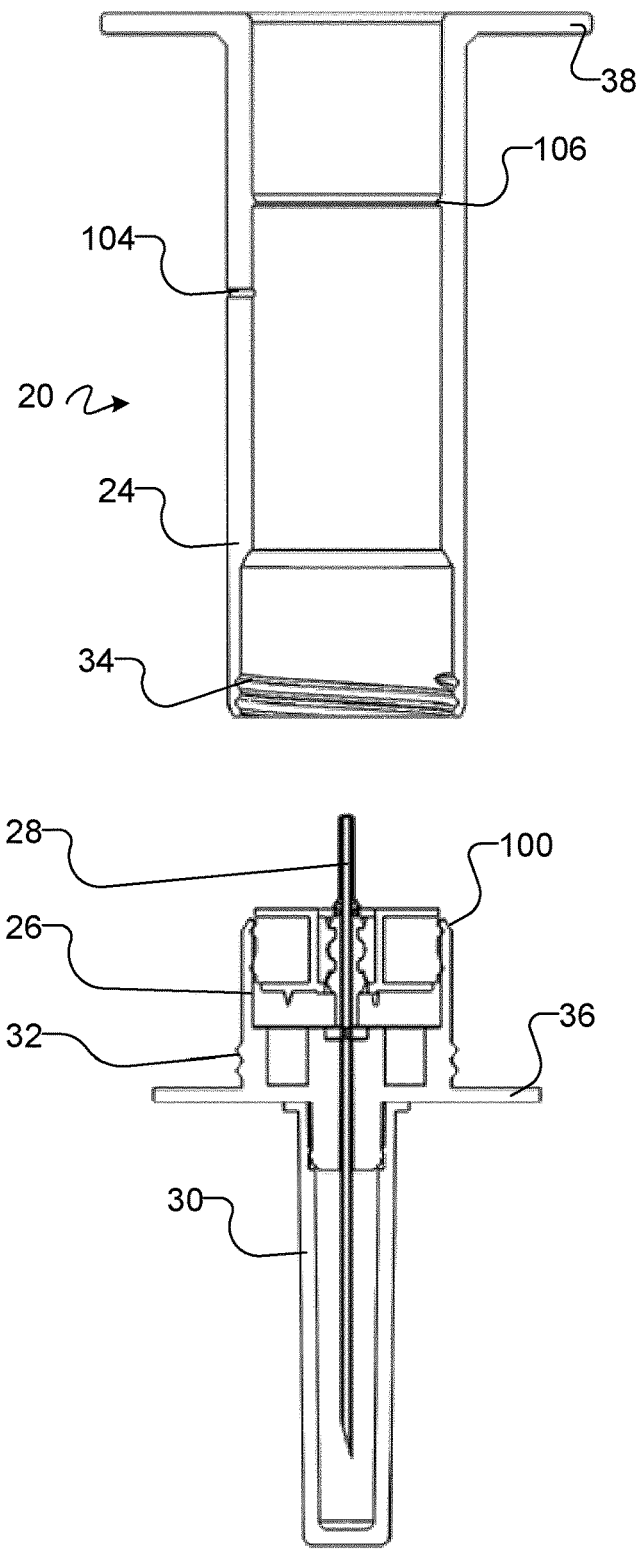
FIG. 3 is a cross-sectional view of the example embodiment of FIG. 2.

An external cap 30 (FIGS. 2 and 3) is provided to cover needle 28 prior to use of retractable blood collection device 20. Cap 30 can be laminated, cemented, snapped, press fit, or otherwise suitably affixed to needle assembly 26 so that it can be removed when retractable blood collection device 20 is ready for use.

In the illustrated embodiment, needle assembly 26 has an external threaded surface 32 (FIG. 2) that is engageable with a complementary threaded internal surface 34 provided in the distal end of main body 24. A radially outwardly extending distal flange 36 provided on needle assembly 26 may facilitate a user inserting needle 28 into a subject from whom blood is to be drawn, and also in gripping needle assembly 26 and affixing it to main body 24 by rotating the two components so that threaded surfaces 32, 34 are engaged when retractable blood collection device 20 is manufactured. A radially outwardly extending proximal flange 38 provided at the proximal end of main body 24 facilitates handling of retractable blood collection device 20 and insertion of a blood collection vial 22 thereon. In some embodiments, flanges 36 and/or 38 are omitted.

In some embodiments, needle assembly 26 is laminated, cemented, snapped, press fit, ultrasonically welded, or otherwise suitably affixed to main body 24 in some other manner during manufacture to provide a single unit. In some such embodiments, flanges 36 are omitted. In some embodiments, a suitable adhesive is applied over threaded surfaces 32 and/or 34, so that after these threaded surfaces have been engaged, the needle assembly 26 cannot thereafter be removed from the main body 24.

Figure 4:
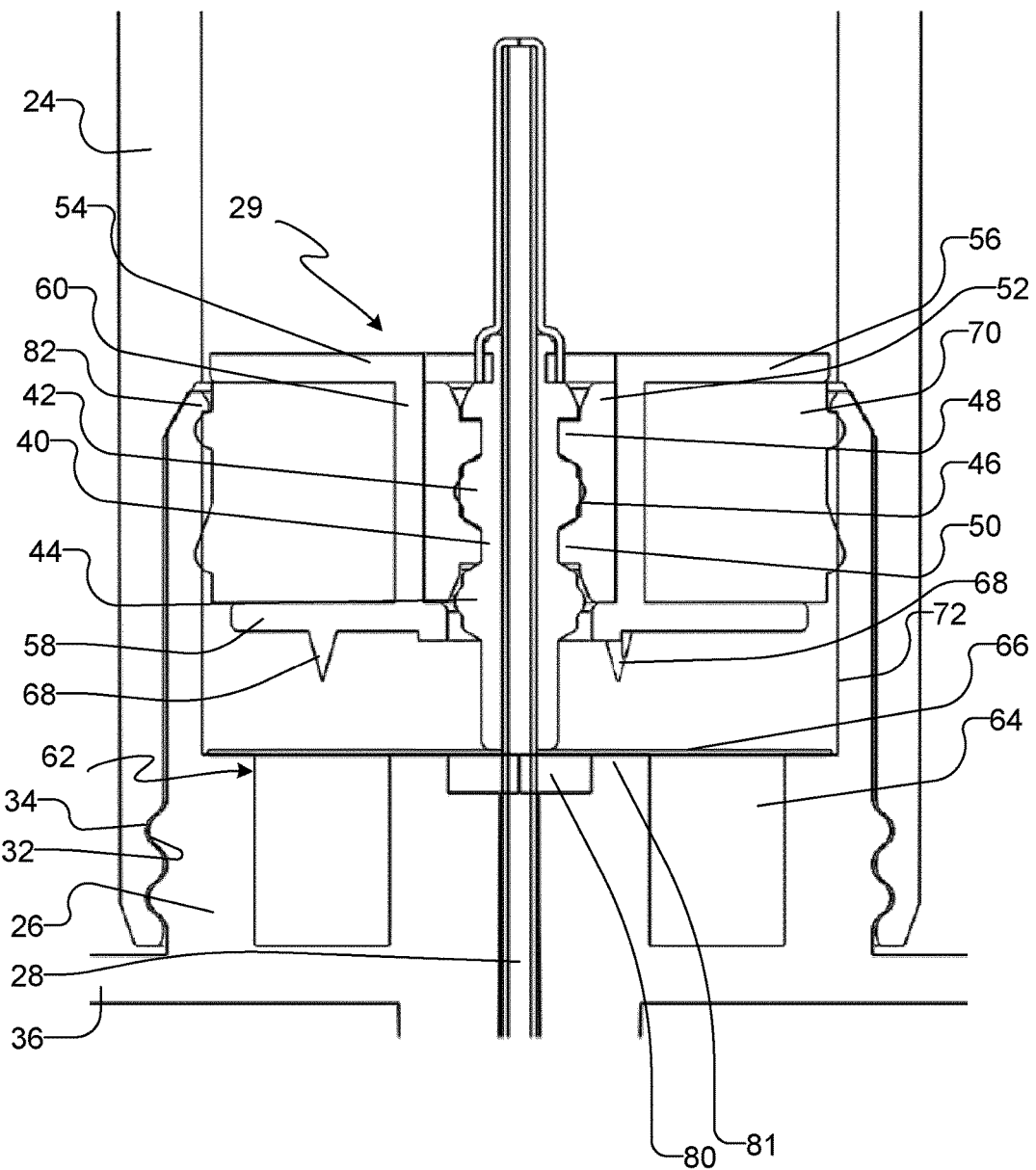
FIG. 4 shows an enlarged partial cross sectional view of the example embodiment of FIG. 2.

With reference to FIG. 4, details of the construction of the needle assembly 26 of the example embodiment are shown and described in more detail. Needle assembly 26 contains a needle retraction assembly 29 for retracting the needle 28. In the illustrated embodiment, the needle retraction assembly comprises a spike plate ring 54, a retraction seal 70, a retaining ring 52, and a needle hub 40. Each of these components is described in greater detail below.

Needle 28 is supported in its initial position relative to needle retraction assembly 29 by a needle hub 40. Needle 28 is crimped in, cemented to or otherwise securely fixed to needle hub 40. In some embodiments, needle 28 is insert molded with needle hub 40 to create a single part.

Figure 9:
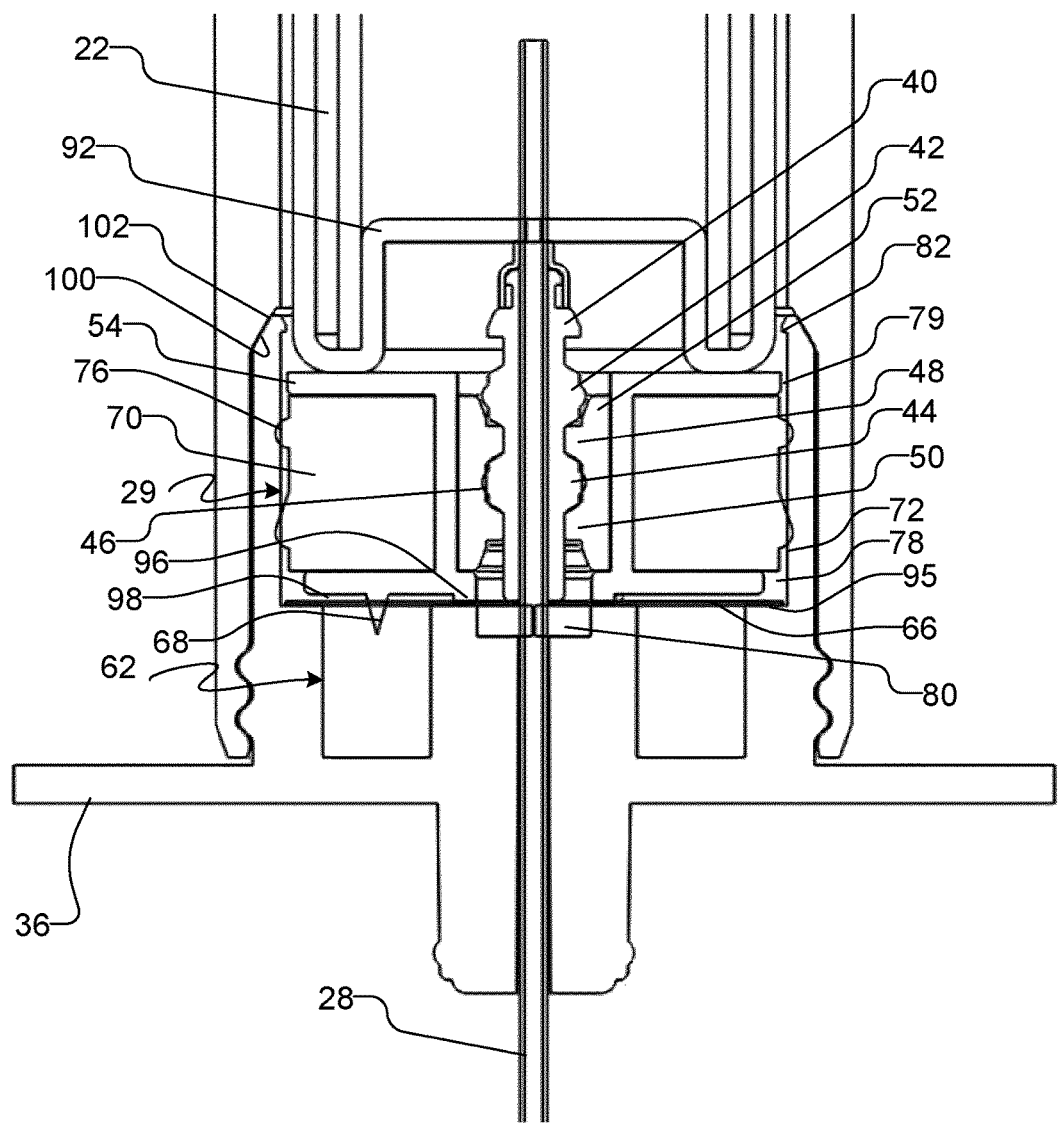
FIG. 9 shows an enlarged partial cross-sectional view of the example embodiment of FIG. 6, but with the blood collection vial moved to the activated position.

Needle hub 40 is moveable relative to the other components of needle retraction assembly 29 between a first sealed position when needle retraction assembly 29 is in its initial assembled position (e.g. as shown in FIG. 4), and a second sealed position when needle retraction assembly 29 is in its activated position (e.g. as shown in FIG. 9). To achieve this, in the illustrated embodiment, needle hub 40 is provided with a first radial sealing feature 42 and a second radial sealing feature 44. First radial sealing feature 42 is initially engaged within a retaining recess 46 formed between two radially inwardly extending arms 48, 50 of a retaining ring 52 of needle retraction assembly 29. Both first radial sealing feature 42 and second radial sealing feature 44 are configured to be sealingly engageable within retaining recess 46, as described in greater detail below. Thus, needle hub 40 is moveable relative to the other components of needle retraction assembly 29 between a first position in which the first radial sealing feature is engaged with another component of retraction assembly 29 (the initial assembled position) and a second, sealed, position in which the second radial sealing feature is sealingly engaged with another component of retraction assembly 29 (the activated position).

While in the description herein first and second radial sealing features 42 and 44 have been described as being substantially the same, these features need not be the same. Further, it is not essential that first radial sealing feature 42 be sealingly engaged with retaining recess 46 in the initial assembled position. At the times that first radial sealing feature 42 is engaged with retaining recess 46 (i.e. in the initial assembled position), all that is required is that the first radial sealing feature 42 prevent movement of needle hub 40 (and thus needle 28) relative to the other components of needle retraction assembly 29, for example while needle 29 is being inserted into and/or withdrawn from a subject and while blood is being drawn. However, after a user has initiated activation of the retraction mechanism but before spikes 68 have moved a sufficient distance in the distal direction that rupture of seal 66 is likely, first radial sealing feature 42 should provide a sealing engagement with retaining ring 52 as needle hub 40 is moved proximally relative to the other components of needle retraction assembly 29 (including retaining ring 52).

This sealing engagement once initiated, together with the engagement of second radial sealing feature 42 with retaining ring 52, provides a substantially continuous sealing engagement between needle hub 40 and retaining ring 52 as needle hub 40 is moved farther in the proximal direction relative to retaining ring 52 to its activated position, as described in more detail below. In the illustrated embodiment, first radial sealing feature 42 is sealingly engaged with retaining recess 46 in the initial assembled position, and together with second radial sealing feature 44 provides a substantially continuous sealing engagement between needle hub 40 and retaining ring 52 as needle retraction assembly 29 moves from its initial assembled position to its activated position.

In the illustrated embodiment, retaining ring 52 is supported by a spike plate ring 54. Spike plate ring 54 is generally cylindrical in shape, and has an upper flange 56 and a lower flange 58 connected by a central ring 60 extending therebetween. Retaining ring 52 is seated inside central ring 60 and does not move relative to central ring 60 during use or retraction of retractable blood collection device 20.

In some embodiments, spike plate ring 54 is made of a relatively rigid material, for example a relatively rigid polymer such as polycarbonate, Styrolux™, polypropylene, or the like, and retaining ring 52 is formed from a relatively more flexible material, such as an elastomer such as a thermoplastic elastomer. The material used to form retaining ring 52 should be sufficiently flexible to allow first radial sealing feature 42 to be displaced therefrom and second radial sealing feature 44 to be inserted therein during retraction of needle 28, as described below, but should also have sufficient rigidity to hold needle hub 40 in place during normal use, for example during insertion of needle 28 into a subject.

In some embodiments, retaining ring 52 is provided as an overmold on spike plate 54. However, spike plate ring 54 and retaining ring 52 can be provided as two separate components coupled together in any suitable manner, for example by a sufficiently tight friction fit, through the use of suitable adhesives, by provision of mechanical interlocks, or the like.

To power the retraction of needle 28, a propellant chamber 62 is provided within needle assembly 26. In the illustrated embodiment, propellant chamber 62 is provided distally of spike plate ring 54, and is formed as a generally cylindrical channel 64 formed within the body of needle assembly 26 and covered by a seal 66. A compressed propellant is contained within propellant chamber 62 by seal 66. Any suitable propellant can be used, for example a medical grade propellant such as a hydrofluorocarbon such as heptafluoropropane or 1,1,1,2-tetrafluoroethane, or medical grade nitrogen.

To release compressed propellant from propellant chamber 62, spike plate ring 54 is provided with one or more spikes 68, which rupture seal 66 when retraction of needle 28 is initiated by a user as described below.

Figure 5:
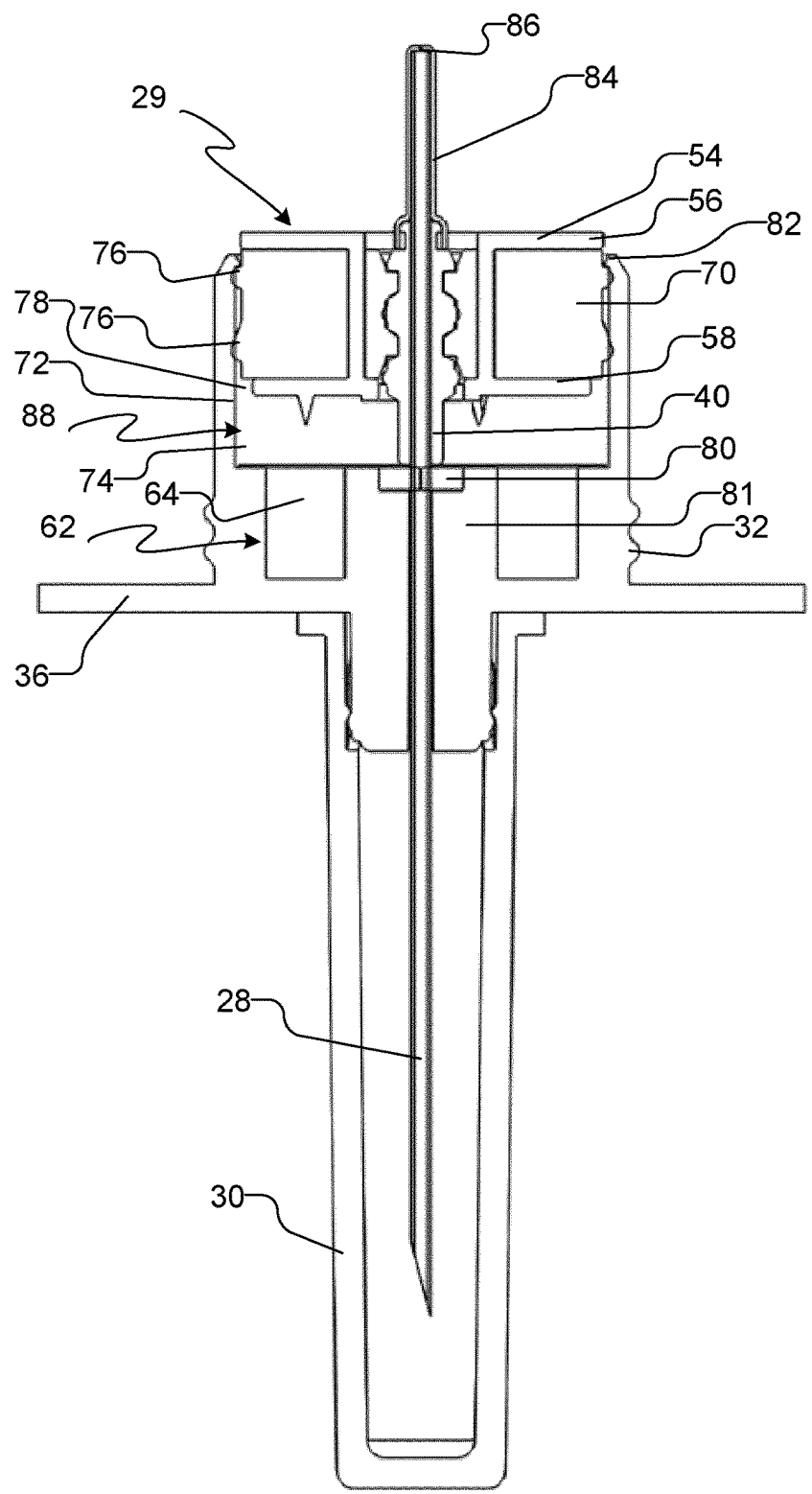
FIG. 5 shows a cross-sectional view of the needle assembly of the example embodiment of FIG. 2.

With reference to FIG. 5, to facilitate movement of spike plate ring 54 within needle assembly 26 when needle 28 is retracted, a retraction seal 70 is provided that is frictionally initially engaged with the sidewall 72 of the upper chamber 74 of needle assembly 26. Retraction seal 70 is slideable in the distal direction within upper chamber 74 in response to the application of an activation force by a user. In the illustrated embodiment, retraction seal 70 has a pair of outwardly extending O-ring seals 76 integrally formed therewith. O-ring seals 76 make sealing engagement with the inside surfaces of sidewall 72. Provision of a pair of O-ring seals 76 spaced apart in the axial direction on retraction seal 70 helps to ensure that retraction seal 70 slides evenly and smoothly within upper chamber 74.

Retraction seal 70 is associated with spike plate ring 54 as part of the needle retraction assembly 29. In the illustrated embodiment, retraction seal 70 is seated inside of spike plate ring 54, being axially retained between upper flange 56 and lower flange 58 of spike plate ring 54. In this fashion, distal movement of spike plate ring 54 caused by the application of an activation force by a user causes retraction seal 70 (and thus needle retraction assembly 29) to slide distally within upper chamber 74, advancing spikes 68 towards seal 66. While one specific exemplary configuration has been described, any suitable configuration that allows retraction seal and spike plate ring 54 to be moved distally to rupture seal 66 and proximally to retract needle 28 could be used.

Retraction seal 70 can be made from any suitable material, for example silicone or an elastomer such as a thermoplastic elastomer. In some embodiments, retraction seal 70 is formed as an overmold on spike plate ring 54. In some embodiments, retraction seal 70 is formed as a separate component from spike plate ring 54, and is coupled to spike plate ring 54 in any suitable manner, for example by cutting axially through one portion of retraction seal 70 so that retraction seal 70 can be inserted over central ring 60, by forming retraction seal 70 as a ring and forming spike plate ring 54 as two separate pieces (e.g. with lower flange 58 and central ring 60 as one piece, and upper flange 56 as a separate piece) so that retraction seal 70 can be inserted over central ring 60 and then retained therein by subsequently securing upper flange 56 to central ring 60 in any suitable manner, for example by use of a suitable adhesive, suitable welding techniques, or the like.

Figure 8:
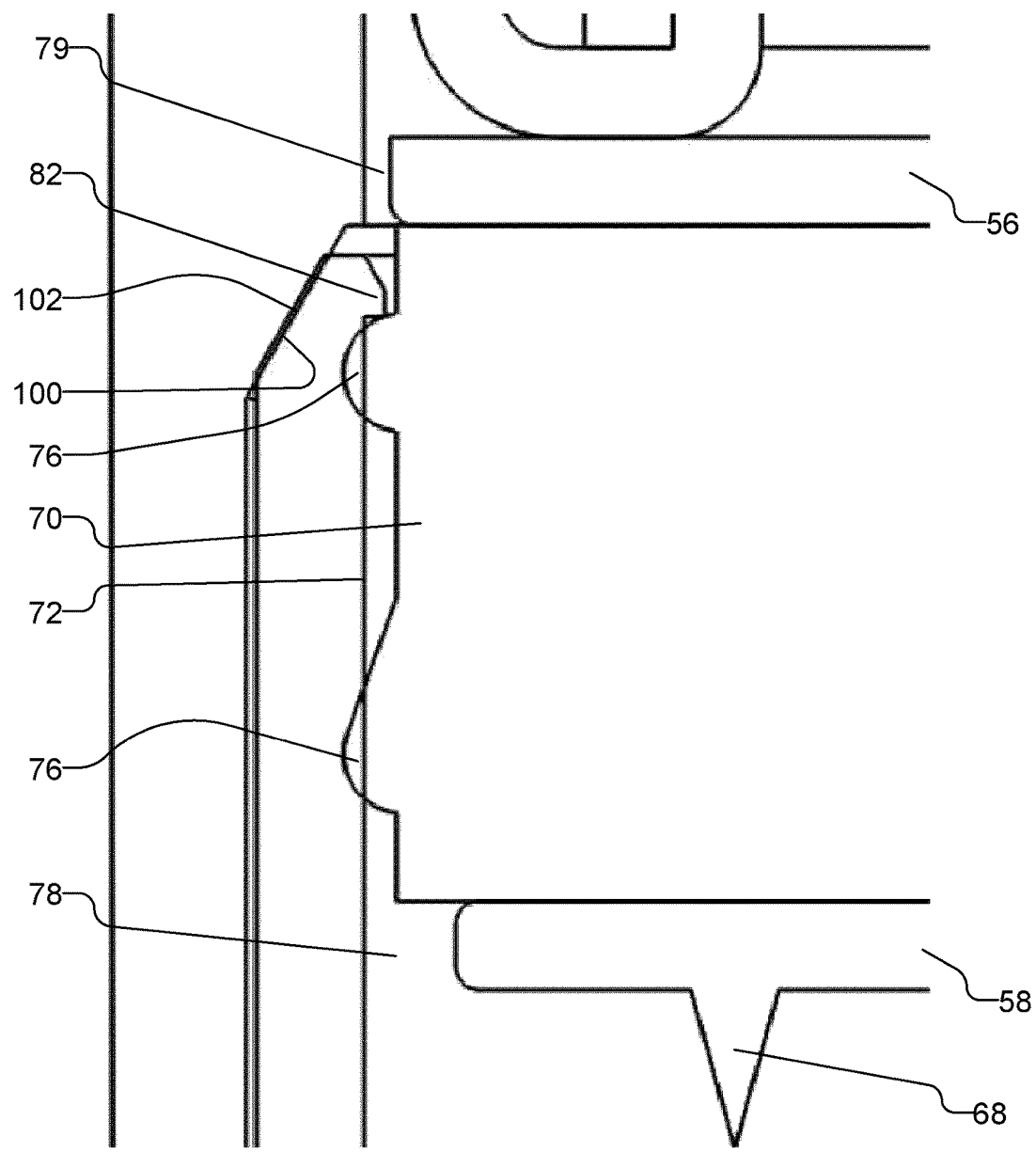
FIG. 8 shows a further enlarged partial cross-sectional view of the example embodiment of FIG. 6.

In the illustrated embodiment, there is a slight inset gap 78 between the radially outer edge of lower flange 58 and the inside surface of sidewall 72 and a similar inset gap 79 (best seen in FIG. 8) between the radially outer edge of upper flange 56 and the inside surface of sidewall 72. The inset gaps do not need to be as large as that illustrated for inset gap 78, although they can be that large or larger. However, the inset gaps 78, 79 should be sufficiently large that upper and lower flanges 56, 58 will not impinge on a radially inwardly extending projection 82 provided on the upper edge of sidewall 72 when spike plate ring 54 moves in the proximal direction during retraction of needle 28.

Projection 82 is a radially inwardly extending projection provided on the inside surface of sidewall 72 to prevent retraction seal 70 (and therefore the other components of needle retraction assembly 29, as well as needle 28) from moving in the proximal direction during normal use of retractable blood collection device 20. However, projection 82 is configured to allow retraction seal 70 to slide past projection 82 in the proximal direction under the force applied by released propellant when the retraction mechanism of device 20 is actuated. In some embodiments, projection 82 comprises one or more discrete projections formed in the inside surface of sidewall 72. In some embodiments, projection 82 comprises a generally circular projection that extends continuously or substantially continuously around the inner diameter of sidewall 72. The exact configuration used for projection 82 is not critical, so long as it initially retains needle retraction assembly 29 in place during normal use of retractable blood collection device 20 to collect blood, but allows needle retraction assembly 29 to slide past in the proximal direction after the retraction mechanism has been actuated by a user.

In the illustrated embodiment, upper chamber 74 of needle assembly 26 is generally cylindrical in shape, and retraction seal 70 and spike plate ring 54 similarly have a generally cylindrical shape. Because blood collection vials and blood collection devices have a generally cylindrical configuration, a corresponding cylindrical shape of components of blood collection device 20 is typical. However, nothing prevents the use of other shapes of components (e.g. having a triangular, square, or irregular cross-section across an axial length thereof), so long as such changes in shape do not affect the ability of the components to move relative to one another to achieve retraction of needle 28 as described herein.

To assist in retaining released propellant within a propellant release chamber 88 defined by the inside surface of sidewall 72, retraction seal 70, propellant chamber 62, needle hub 40 and retaining ring 52, in some embodiments a distal needle seal 80 is provided to seal around needle 28 at the distal end of upper chamber 74. In the illustrated embodiment, distal needle seal 80 is secured within a central region 81 of the body of needle assembly 26 that is provided axially inwardly of generally cylindrical channel 64. Distal needle seal 80 is made from a soft material to sealingly engage around the outside surface of needle 28 and prevent the flow of propellant past needle 28 and out of the propellant release chamber 88.

To prevent blood from flowing through needle 28 when a blood collection vial 22 is not installed on retractable blood collection device 20, a proximal needle seal 84 is provided to cover the proximal end of needle 28. The portion of proximal needle seal 84 that covers the proximal end of needle 28 has a small aperture therethrough, indicated by 86, that allows proximal needle seal 84 to open around the proximal end of needle 28 when a blood collection vial 22 is inserted on retractable blood collection device 20. Proximal needle seal 84 thus acts as a sheath, to cover the proximal end of needle 28 to prevent the flow of blood therethrough when a blood collection vial 22 is not inserted on retractable blood collection device 20, but to allow blood to flow therethrough when a blood collection vial 22 is in use. This feature is useful where more than one vial of blood is to be collected from a patient.

With reference again to FIG. 1, in use with needle assembly 26 coupled to main body 24, after external cap 30 has been removed and the needle 28 of needle assembly 26 has been inserted into a subject from whom blood is to be drawn in a conventional manner, proximal needle seal 84 will prevent the flow of blood through needle 28 until a blood collection vial 22 is inserted inside main body 24 of retractable blood collection device 20.

Figure 6:
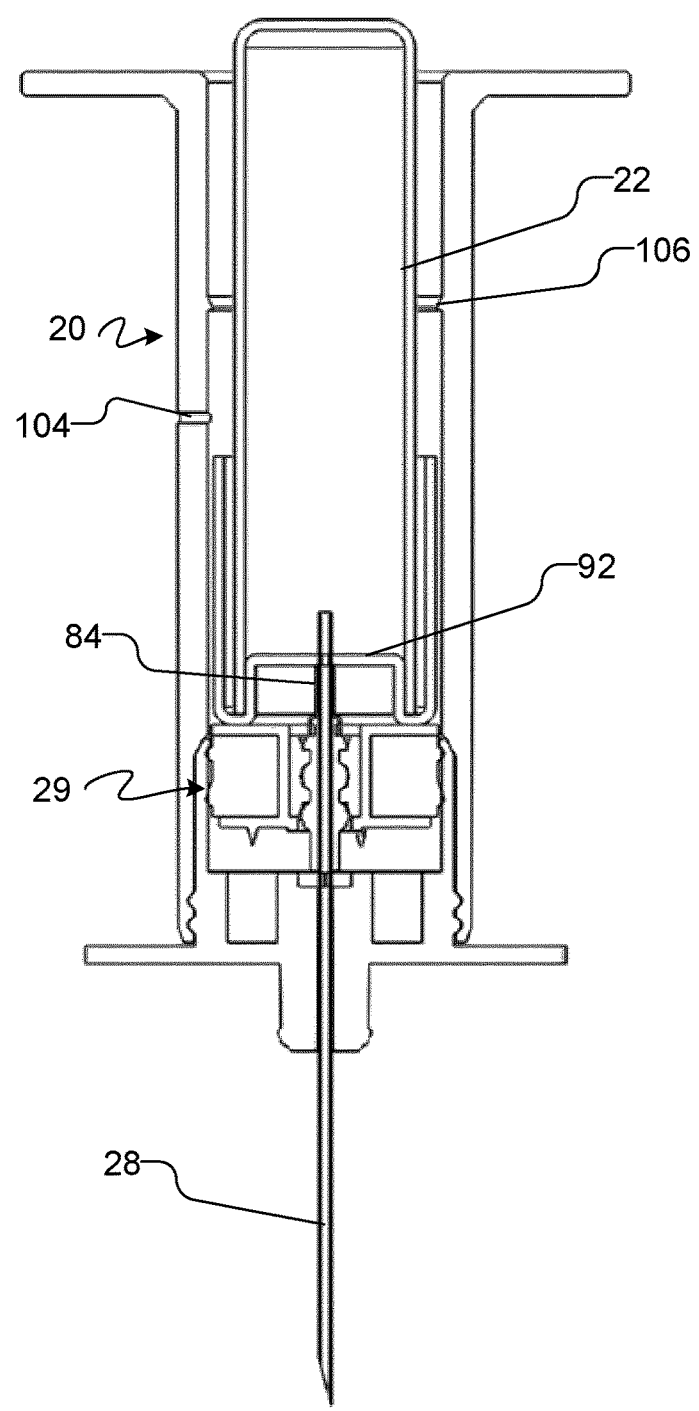
FIG. 6 shows a cross-sectional view of the example embodiment of FIG. 2, with a blood collection vial inserted thereon in its initial assembled position.
Figure 7:
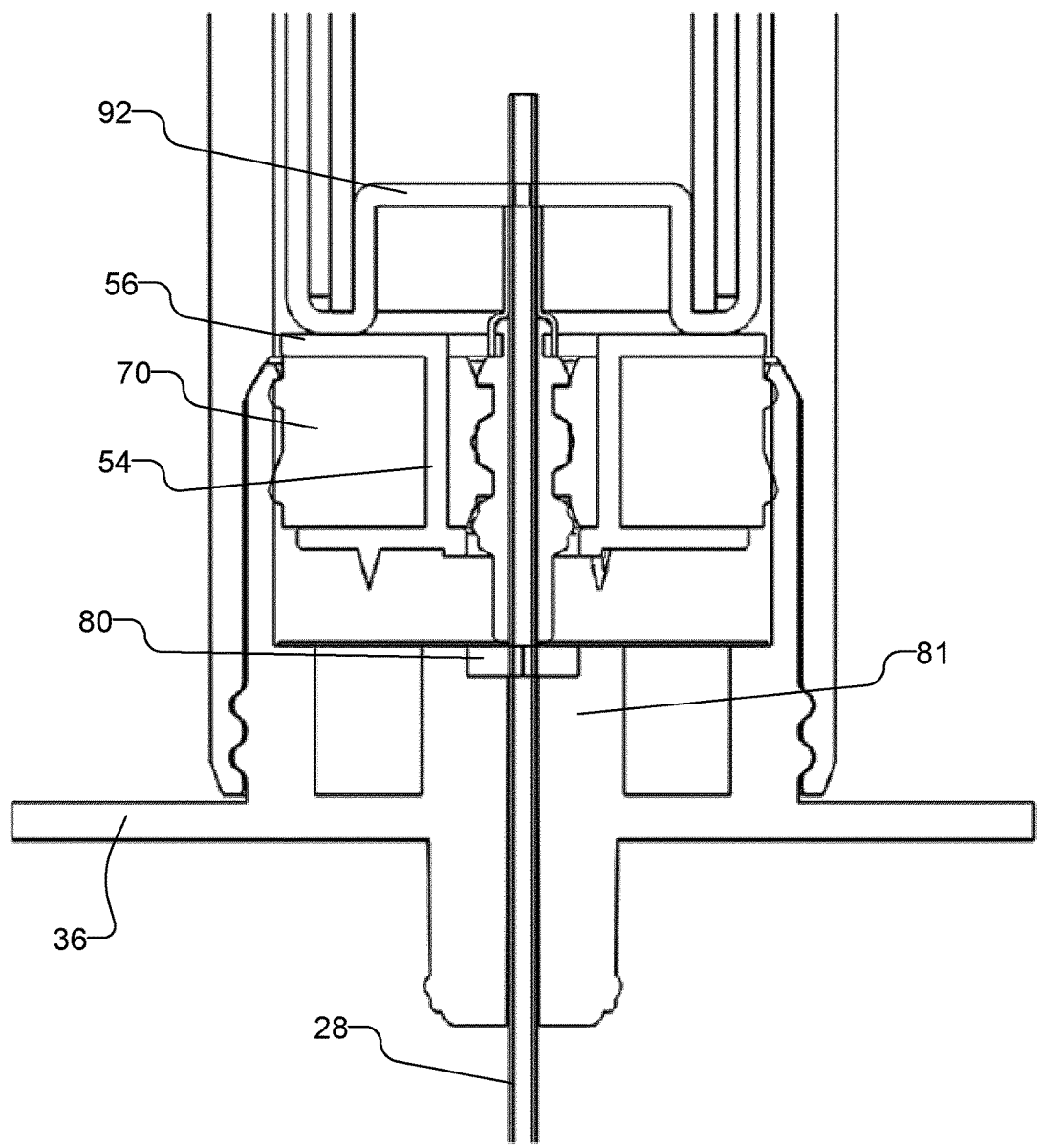
FIG. 7 shows an enlarged partial cross-sectional view of the example embodiment of FIG. 6.

Blood collection vial 22 has a tube 90 for receiving and containing blood, and a cover 92 for retaining blood within tube 90. Cover 92 has a central portion made from a flexible material that has a small aperture 94 therethrough. Cover 92 is configured so that aperture 94 can be inserted over the proximal end of needle 28, thereby displacing proximal needle seal 84 from the proximal end of needle 28, as shown in FIGS. 6 and 7. Aperture 94 is sufficiently small that a drop of liquid (e.g. blood) cannot pass therethrough when aperture 94 is not expanded around needle 28. Thus, blood is securely retained within tube 90 once it has been obtained.

Blood collection vial 22 can be inserted within main body 24 of retractable blood collection device 20 from the proximal end until it reaches an initial assembled position immediately adjacent upper flange 56 of spike plate ring 54. At this point, a user will feel resistance to further movement of blood collection vial 22 in the distal direction because of the engagement of retaining ring 52 with first radial sealing feature 42 of needle hub 40 (needle hub 40 being prevented from moving in the distal direction by reason of the contact of its distal end with central region 81, optionally via distal needle seal 80) as well as because of the frictional engagement of O-ring seals 76 of retraction seal 70 with the inside of sidewall 72. A user will thus know that blood collection vial 22 has reached its initial assembled position.

Once vial 22 has been filled with blood, a user can optionally withdraw vial 22 from retractable blood collection device 22. Removal of cover 92 from the proximal end of needle 28 will result in proximal needle seal 84 moving in the proximal direction and once again covering the proximal opening of needle 28, so that blood will not flow therethrough while no vial 22 is attached. A user can then insert a fresh vial 22 onto retractable blood collection device 22, and can fill that vial 22 with blood. This process can be repeated any desired number of times, depending on the number of vials of blood that need to be collected from a given subject.

When a user reaches the last required vial 22 for a given subject, the user can actuate the retraction mechanism to retract needle 28 within main body 24 to eliminate the sharps hazard posed by needle 28. Depending on user preferences and applicable regulatory requirements, in some embodiments, the retraction mechanism can be actuated while needle 28 remains in the subject. In other embodiments, needle 28 is removed from the subject, and then a user actuates the retraction mechanism to retract needle 28.

FIG. 9 illustrates how the retraction mechanism is actuated. A user presses vial 22 in the distal direction beyond its initial assembled position, optionally using proximal flange 38 and/or distal flange 36 to assist in this process. Because the distal end of needle hub 40 is in contact with central region 81 (including optionally being in contact with distal needle seal 80), needle hub 40 cannot move in the distal direction in response to the applied force. However, the other components of the retraction assembly 29 are moved in the distal direction by this force. Retraction seal 70 is slideable within sidewall 72 in response to the applied force. Retaining ring 52 is made of a somewhat flexible material, and thus radially inwardly extending arm 50 can flex as it moves past second radial securing feature 44, and radially inwardly extending arm 48 can likewise flex as it moves past first radial securing feature 42. The components of needle retraction assembly 29 other than needle hub 40 (i.e. retaining ring 52, spike plate ring 54, and retraction seal 70) are thus caused to move in the distal direction within propellant release chamber 88 when a user applies sufficient force to actuate the retraction mechanism.

The components of retractable blood collection device 20 should be designed so that the additional force required to actuate the retraction mechanism (i.e. to move vial 22 in the distal direction beyond its initial assembled position) is not unduly large, or users will have a difficult time actuating the retraction mechanism. However, the force required to actuate the retraction mechanism should be designed to be sufficiently large that it is unlikely that a user will inadvertently cause actuation of the retraction mechanism during ordinary use of retractable blood collection device 20. Factors such as the hardness (e.g. durometer) of the material used to manufacture retaining ring 52 or retraction seal 70 and the shaping and configuration of radially inwardly extending arms 48, 50 and/or first and second radial sealing features 42, 44 can all influence the amount of force that will be required to actuate the retraction mechanism of device 20.

As illustrated in FIG. 9, continued movement of retaining ring 52, spike plate ring 54, and retraction seal 70 in the distal direction to the activated position moves first radial sealing feature 42 of needle hub 40 out of retaining recess 46 of retaining ring 52, and causes second radial sealing feature 44 of needle hub 40 to become sealingly engaged within retaining recess 46. Thus, needle hub 40 remains sealingly engaged with retaining ring 52, even after spike plate ring 54 has been moved from its initial assembled position to the activated position.

Further movement of retaining ring 52, spike plate ring 54 and retraction seal 70 in the distal direction causes spikes 68 to come into contact with and rupture seal 66. Rupture of seal 66 releases propellant from generally cylindrical channel 64 into propellant release chamber 88.

The design of needle hub 40 and retaining ring 52 is such that a seal between needle hub 40 and retaining recess 46 is formed before seal 66 is ruptured, even if needle hub 40 and retaining ring 52 have not been moved fully to the activated position. This prevents the escape of propellant past needle hub 40, which might result in a failure of the needle retraction assembly 29 to retract. In the illustrated embodiment, a seal is formed between second radial sealing feature 44 and retaining ring 52 so that these two components are continuously sealed even during relative movement of these components, which prevents passage of propellant past needle hub 40 even if seal 66 is ruptured before radial sealing feature 44 is fully seated in retaining recess 46. By "continuously sealed" it is not meant that the location of the seal is substantially continuous, but rather that temporally as needle hub 40 moves relative to retaining ring 52, there is a seal at some location between these two elements at all times from a first time before seal 66 is reasonably likely to be ruptured to a second time when radial sealing feature 44 becomes fully seated in retaining recess 46.

To prevent formation of a seal between the outside lip 95 of propellant chamber 62 and spike plate ring 54, a distal axially extending flange 96 is provided at the distal end of spike plate ring 54. Flange 96 contacts the proximal end of central region 81 and/or distal needle seal 80, which ensures that at least a small gap 98 remains between lower flange 58 and the outside lip 95 of propellant chamber 62, so that no seal is formed between lower flange 58 and the outside lip 95 of propellant chamber 62.

In some embodiments, including the illustrated embodiment, flange 96 is substantially circular, so that flange 96 forms a seal with the proximal end of central region 81 (and/or distal needle seal 80, depending on the relative positioning of needle seal 80). Formation of a seal between flange 96 and central region 81 as aforesaid can minimize the amount of pressure applied by released propellant against needle hub 40. This provides a safeguard or additional level of sealing in the event that seal 66 is ruptured before second radial sealing feature 44 has been fully engaged within retaining recess 46, and also helps to ensure that second radial sealing feature 44 will be fully seated in retaining recess 46 as the needle retraction assembly 29 moves in the proximal direction. Accordingly, the sealing engagement between flange 96 and the proximal end of central region 81 provides a feature that is used in some embodiments to minimize the risk that needle 28 will not reliably retract.

The released propellant applies a force in the proximal direction against retraction seal 70 to retract needle retraction assembly 29 and needle 28. Spike plate ring 54, retaining ring 52, needle hub 40, and blood collection vial 22 are all moved in the proximal direction by movement of retraction seal 70. As described above and as best seen in FIG. 8, inset gaps 78, 79 are sufficiently large to ensure that upper flange 56 and lower flange 58 pass by radially inwardly extending projection 82 when spike plate ring 54 moves in the proximal direction.

The material used to provide retraction seal 70 is selected to be sufficiently flexible to allow O-ring seals 76 to pass by radially inwardly extending projection 82 when retraction seal 70 is moved in the proximal direction by the force of released propellant. However, the material used for retraction seal 70 should also be selected to provide a sufficient degree of resistance to passage over radially inwardly extending projection 82 such that forces experienced during normal use of retractable blood collection device 20 to collect blood (including insertion of needle 28 into a subject from whom blood is to be drawn) do not force retraction seal 70 past radially inwardly extending projection 82. For example, in one example embodiment, it is anticipated that retraction seal 70 might experience approximately 1-2 lbs of force in the proximal direction during insertion of a needle 28 into a subject, and retraction seal 70 is designed not to move past radially inwardly extending projection 82 until a force in the proximal direction of at least 3-4 lbs is applied. In such example embodiment, the force expected to be applied against retraction seal 70 by released propellant is anticipated to be on the order of 9-10 lbs or more, so that retraction seal 70 will be reliably retracted past radially inwardly extending projection 82 upon actuation of the retraction mechanism.

To assist in containing released propellant within propellant release chamber 88, in some embodiments including the illustrated embodiment, a pair of complementary angled sealing surfaces 100, 102 (FIG. 8) are provided at the proximal end of needle assembly 26 and the distal portion of main body 24, respectively. The engagement of threaded surfaces 32, 34 forces angled sealing surfaces 100, 102 tightly together, to help prevent the escape of propellant past the junction between needle assembly 26 and main body 24. In some embodiments, the engagement between needle assembly 26 and main body 24 is sufficiently airtight that angled sealing surfaces 100, 102 are omitted. In some embodiments in which needle assembly 26 and main body 24 are integrally formed or permanently coupled together, e.g. by being laminated, cemented, snapped, press fit, ultrasonically welded, or otherwise joined, the engagement between the two components is airtight or substantially airtight, and angled sealing surfaces 100, 102 can be omitted.

Figure 10:
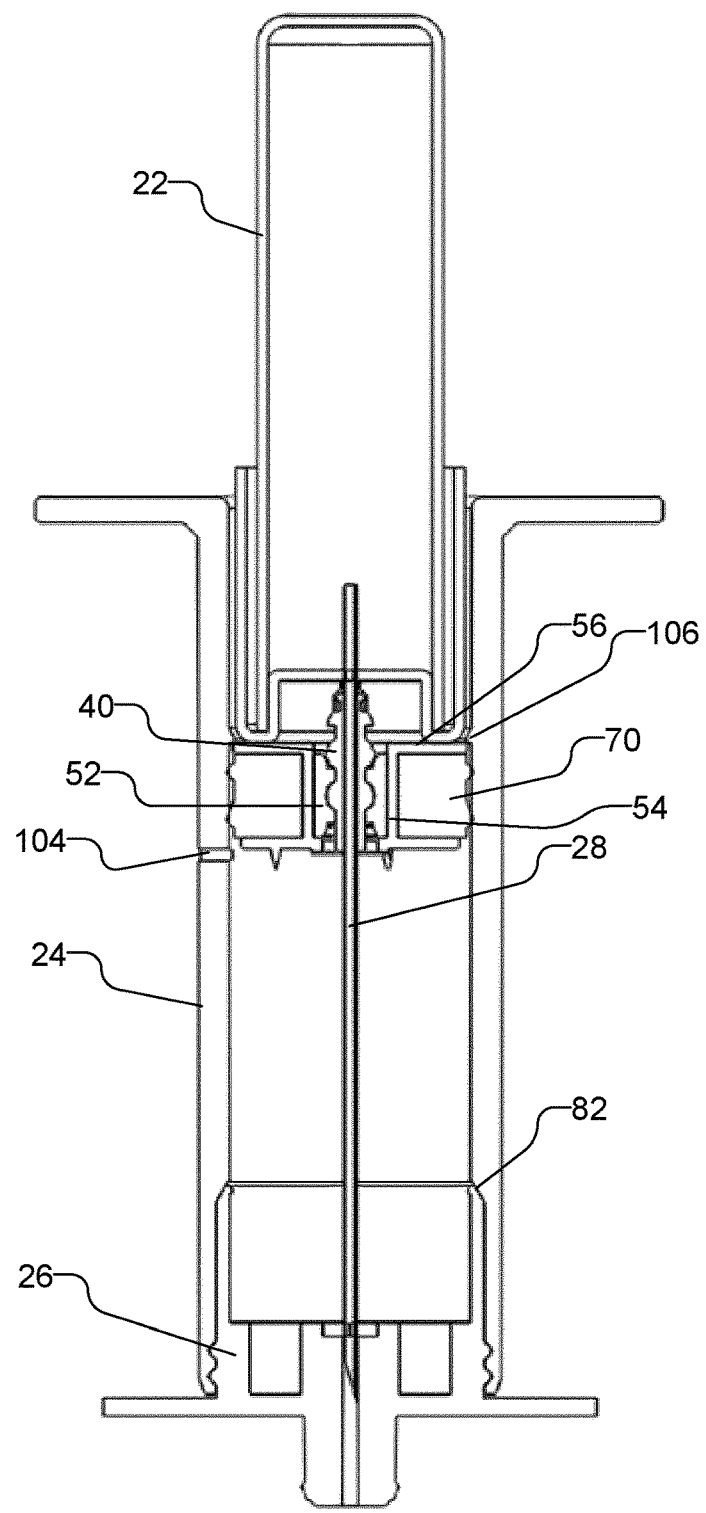
FIG. 10 shows a cross-sectional view of the example embodiment of FIG. 6, with the needle in its final retracted position.

After retraction seal 70 slides proximally over radially inwardly extending projection 82, it continues moving in the proximal direction. To assist in stopping movement of retraction seal 70 (and therefore all of the other components of needle retraction assembly 29 sliding proximally under influence of released propellant) once needle 28 has been retracted to a desired degree (i.e. moved to its final retracted position) as shown in FIG. 10, two features are provided on main body 24. The first of these features is vent 104 provided in a sidewall of main body 24 at an axial location just distal of the final retracted position of retraction seal 70. Vent 104 releases propellant from the interior of retractable blood collection device 20, so that the proximal biasing pressure applied by released propellant is dissipated after retraction seal 70 slides proximally past vent 104. In some embodiments, vent 104 is omitted, and only a stop 106 (described below) is used to stop the proximal movement of retraction seal 70. However, use of vent 104 helps to ensure that no compressed propellant remains within retractable blood collection device 20, meaning that there is no ongoing hazard of a potential release of pressure from device 20 at some undesired future time or in some undesired manner that may cause needle 28 to become exposed.

The second feature provided in the illustrated embodiment to assist in stopping movement of retraction seal 70 (and therefore all of the other components sliding proximally under influence of released propellant) is stop 106. In the illustrated embodiment, stop 106 is a radially inwardly extending projection that extends radially inwardly to a sufficient extent to stop further proximal movement of upper flange 56 of spike plate ring 54 past it at the point of contact. Any structure that can make contact with some portion of the needle retraction assembly 29, including spike plate ring 54, retraction seal 70, needle hub 40 or retaining ring 52, to stop movement of these components past a predetermined point while still allowing blood collection vial 22 to pass could be used to provide the second feature that assists in stopping movement of retraction seal 70. In some embodiments, stop 106 could be omitted, and vent 104 alone could be used to stop movement of the retracting components once needle 28 has been retracted to the desired extent. However, as described below, in some embodiments including the illustrated embodiment, vial 22 is removed by pulling in the proximal direction after needle 28 has been retracted, and stop 106 also acts to prevent unintended withdrawal of retraction seal 70 or any of the components associated therewith, including needle 28, from main body 24. In such embodiments, stop 106 helps to prevent unintended withdrawal of needle 28 from main body 24.

After the needle retraction assembly 29, needle 28 and blood collection vial 22 have been moved to the final retracted position, a user can pull on blood collection vial 22 in the proximal direction to remove the final vial of blood from blood collection device 20. This allows proximal needle seal 84 to slide proximally to cover the proximal end of needle 28. Needle 28 remains safely housed within main body 24 and needle assembly 26, and the used retractable blood collection device 20 can be disposed of in accordance with applicable practices or regulations.

Figure 11:
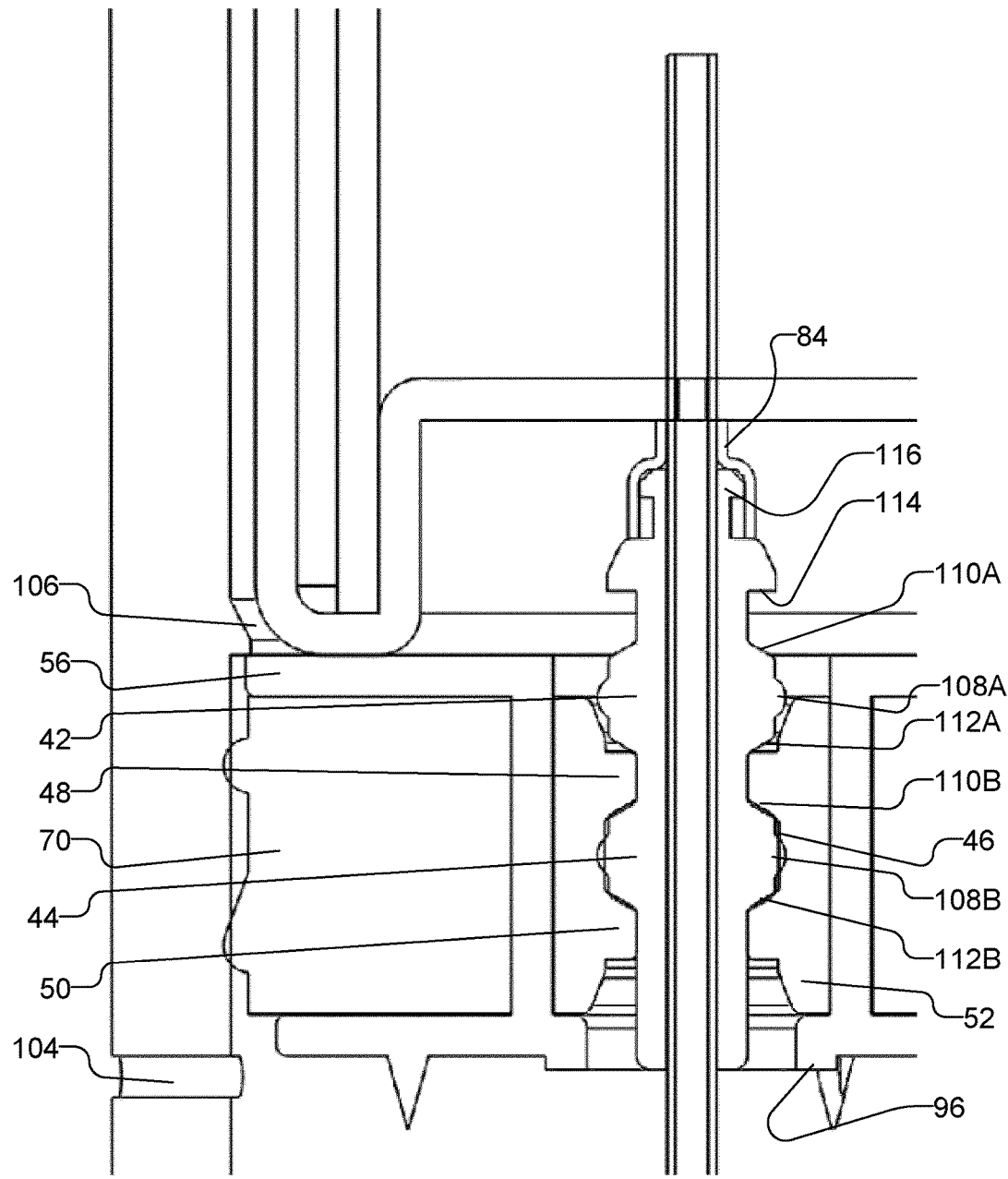
FIG. 11 shows an enlarged partial cross-sectional view of the example embodiment of FIG. 6, with the needle in its final retracted position.
Figure 12:
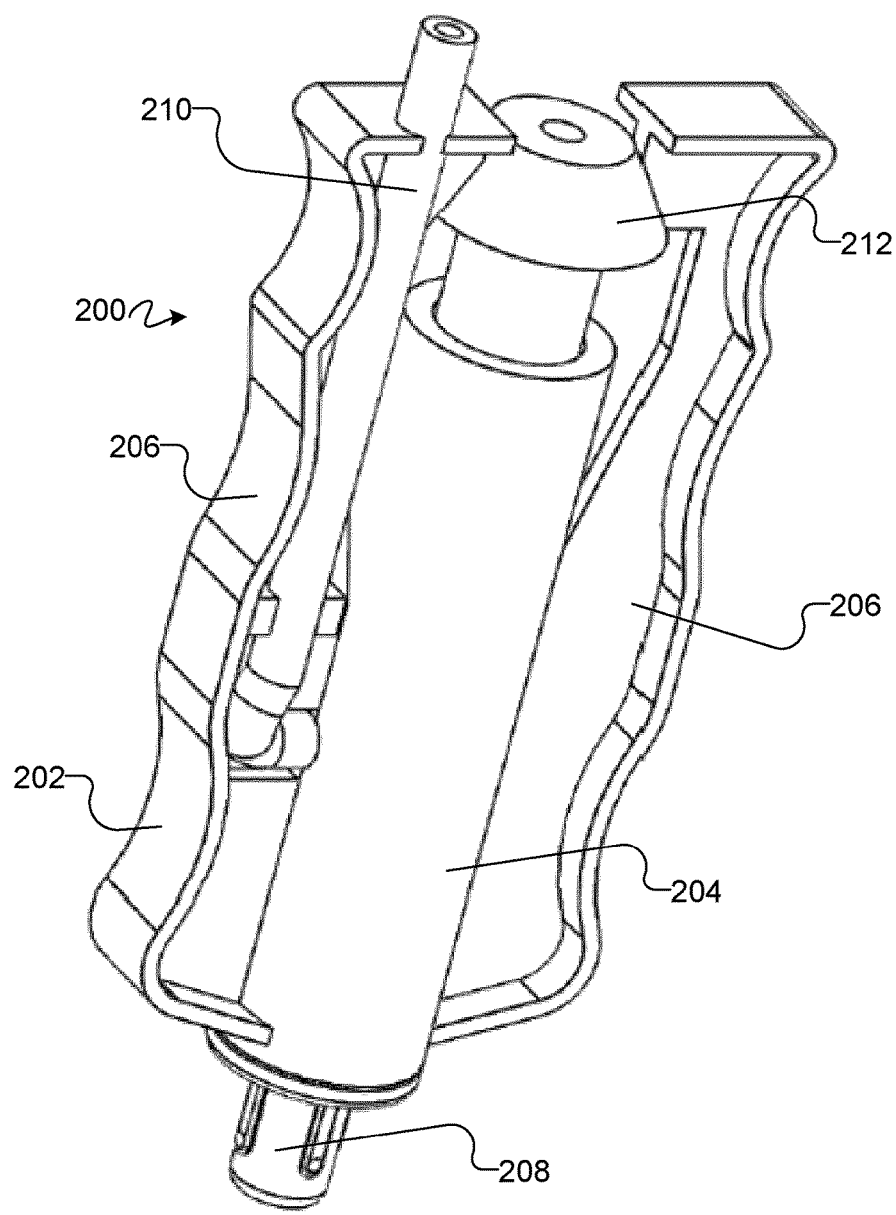
FIG. 12 shows a perspective view of a second example embodiment of a retractable blood collection device, with the needle removed.

With reference to FIG. 11, in some embodiments, including the illustrated embodiment, the structural features of first and/or second radial sealing features 42, 44 that provide a sealing engagement with retaining recess 46 comprise an O-ring seal 108A, 108B, respectively, and two tapered seals 110A, 110B and 112A, 112B, respectively. O-ring seals 108A, 108B and tapered seals 110A, 110B, 112A and 112B are generally cylindrical in shape, and are sealingly engageable with retaining recess 46, which is also generally cylindrical in shape in the illustrated embodiment. Tapered seals 110A/110B are engageable with a correspondingly angled surface provided on radially inwardly extending arm 48, and tapered seals 112A/112B are engageable with a correspondingly angled surface provided on radially inwardly extending arm 50.

While first and second radial sealing features 42, 44 have been described herein as having a particular configuration, any suitable type of sealing engagement that can be axially displaced to allow the first sealing feature to be released from retaining ring 52 and then allow a seal to be formed by the second sealing feature, while providing a substantially continuous sealing engagement before seal 66 is likely to be ruptured, even during sliding motion of needle hub 40 relative to retaining ring 52, can be used. In some embodiments, the structural features of both first and second radial sealing features 42, 44 are the same. In some embodiments, the structural features of both first and second radial sealing features 42, 44 are different, but provide for sealing engagement with retaining recess 46 as the second radial sealing feature 44 becomes engaged within retaining recess 46 and once the second radial sealing feature 44 has reached its activated position (i.e. has been engaged within retaining recess 46).

In the illustrated embodiment, substantially continuous sealing between needle hub 40 and retaining ring 52 is maintained as follows. As second radial sealing feature 44 moves past radially inwardly extending arm 50, O-ring seal 108B will remain in sealing contact therewith, and O-ring seal 108B will also remain sealed against the sidewall of retaining recess 46 as second radial sealing feature 44 moves into retaining recess 46. Once O-ring seal 108B starts to slide into retaining recess 46, tapered seal 112B will make contact with the upper edge of radially inwardly extending arm 50, and will form a seal therewith. After second radial sealing feature 44 has moved fully into retaining recess 46, tapered seal 110B will make contact with and seal against radially inwardly extending arm 48, so that all of tapered seals 110B, 112B and O-ring seal 108B are in sealing engagement with retaining recess 46 when needle retraction assembly 29 is in the activated position.

Needle hub 40 also has an upper retaining flange 114 that prevents needle hub 40 from being pushed distally through retaining ring 52, for example during assembly of retractable blood collection device 20. In the illustrated embodiment, upper retaining flange 114 also provides a stop for proximal needle seal 84 to retract against when proximal needle seal 84 is pulled back during insertion of a blood collection vial 22. In the illustrated embodiment, upper retaining flange 114 projects radially outwardly from the main body of needle hub 40 and sits proximally of and in contact with radially inwardly extending arm 48.

In the illustrated embodiment, needle hub 40 has an upper neck 116. Upper neck 116 provides a point of attachment for securing proximal needle seal 84 over the proximal end of needle 28. The proximal needle seal 84 is stretched over upper neck 116 and secured thereto by the tension created in the material used for proximal needle seal 84.

With reference to FIGS. 12-22, a second example embodiment of a retractable blood collection device 200 is illustrated. Blood collection device 200 has a housing 202 having a central body 204 and a pair of wings 206. A needle assembly 208 is coupled to or integrally formed with central body 204. Blood collection tubing 210 is provided for transferring blood from a subject to any suitable blood collection container. A plunger 212 is slideably mounted within central body 204 for actuating retraction of the needle as described below.

While in some embodiments blood collection device 200 could be used with a blood collection tube such as a Vacutainer™, blood collection device 200 can be used to transfer blood from a subject to any desired blood collection container. Examples of blood collection containers that can be used with some embodiments of blood collection device 200 include blood donation and blood transfusion systems and devices, blood transfer devices, cathethers, intravenous (IV) systems, and the like.

Figure 13A:
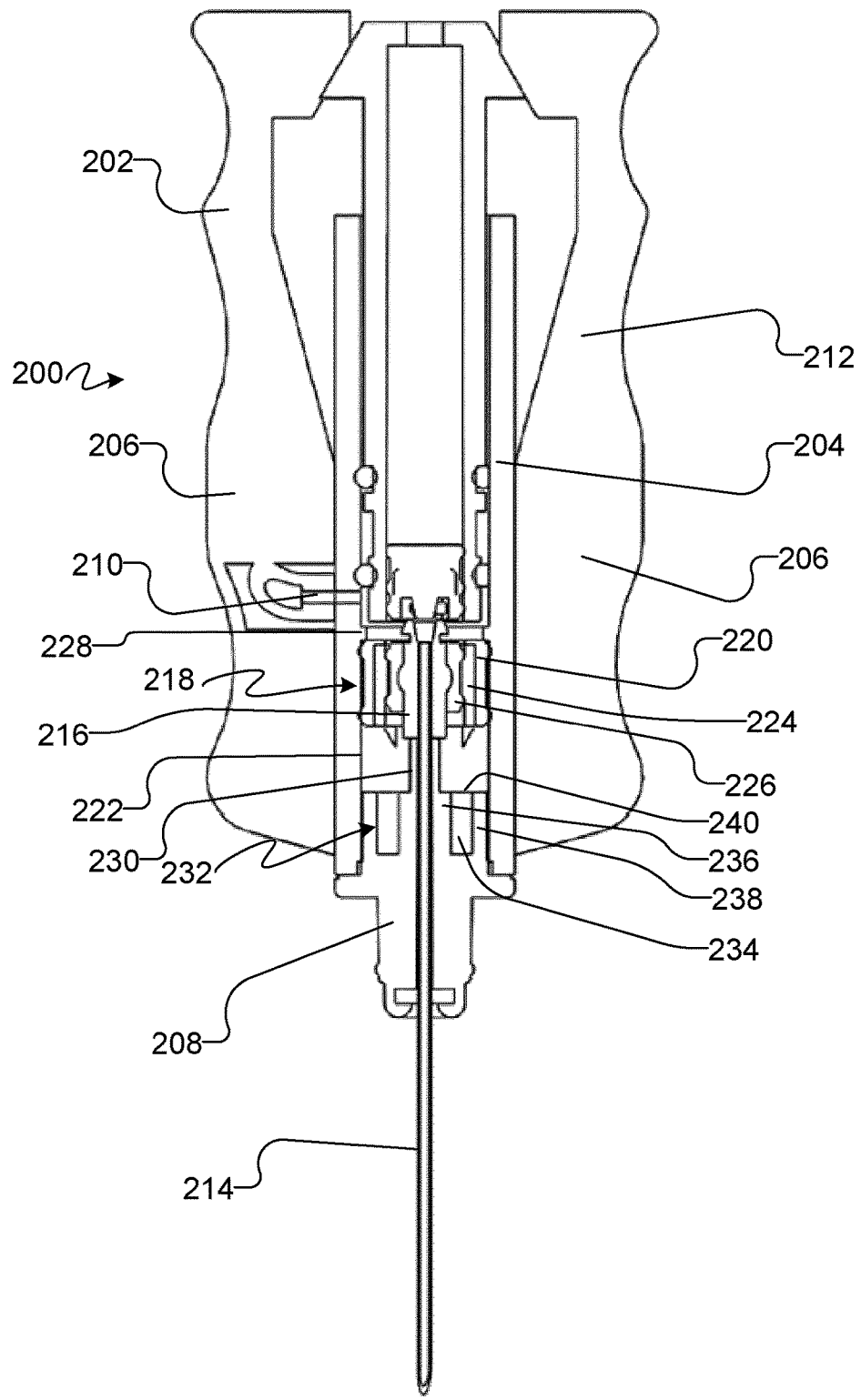
FIG. 13A shows a cross-sectional view of the example embodiment of FIG. 12, with the needle in its initial assembled position.

The internal construction of retractable blood collection device 200 is shown in more detail in FIG. 13A. A needle 214 is provided at the distal end of device 200. A cap or other suitable cover (not shown) can be used to cover needle 214 prior to use of device 200.

Needle 214 is supported in its initial position by a needle hub 216. Needle hub 216 is crimped in, cemented to or otherwise securely fixed to needle hub 216. In some embodiments, needle 214 is insert molded with needle hub 216 to create a single part.

The design of needle hub 216 can be varied. For example in a second example embodiment illustrated in FIG. 13B in which like reference numerals refer to like components, and like reference numerals with the letter A appended thereto refer to equivalent components of the retractable blood collection device 200A, the neck 230 of needle assembly 208A is omitted, and the distal portion of needle hub 216A is lengthened so that it contacts the proximal edge of inner wall 236A. Needle support structure 218A thus supports needle 214 in place in substantially the same way that needle support structure 218 does. In some embodiments, providing a needle assembly 208A with no neck 230 facilitates sealing of seal 240 between inner wall 236A and outer wall 238 during manufacture, since there is a level surface for sealing (i.e. neck 230 is not present to interfere with the positioning of equipment used to form a seal between inner wall 236A, outer wall 238, and seal 240).

Needle hub 216 or 216A is initially supported in position as part of a needle support structure 218 or 218A. In the illustrated embodiments of FIGS. 13A and 13B, and also with reference to the exploded view of FIG. 14, needle support structure 218 or 218A includes needle hub 216/216A and has an external seal 220 in sliding engagement with the interior sidewall 222 of central body 204, a spike plate 224 engaged with and inside of the external seal 220, and an internal seal 226 initially in sealing engagement with the inner surface of the spike plate 224.

The components of needle support structure 218 or 218A can be secured together in any suitable manner which allows the needle retraction assembly 272 (described below) to be formed and retracted. In some embodiments, internal seal 226 is provided as an overmold of an elastomeric material on needle hub 216 or 216A, although these components can be secured together in any suitable manner, for example by sufficiently tight friction fit, the use of suitable adhesives, or the like. In some embodiments, needle hub 216 or 216A is a suitable substrate, for example, plastic, and internal seal 226 is provided as an overmolded elastomer on needle hub 216 or 216A. In the illustrated embodiment, needle hub 216/216A is provided with a central bulge 217 on its outer periphery that engages with a correspondingly shaped recess 219 formed on the inside surface of internal seal 226. The engagement of central bulge 217 and recess 219 helps to retain needle hub 216/216A within internal seal 226.

In some embodiments, central bulge 217 is omitted. In some embodiments in which internal seal 226 is provided as an overmold on needle hub 216/216A, central bulge 217 is omitted. In some embodiments, the shaping of central bulge 217 is varied; for example it may be made asymmetrical or similar in construction to first and second radial sealing features 42, 44. In some such embodiments, the shaping of recess 219 is modified to be complementary to the shaping of central bulge 217, to facilitate central bulge 217 being received in recess 219. In some embodiments, the shaping of central bulge 217 and recess 219 may be selected to more securely hold needle hub 216/216A within recess 219. For example, in one embodiment, the proximal edges of central bulge 217 are provided with a square shape instead of being generally rounded, and the proximal portion of recess 219 is provided with correspondingly squared corners, to provide an even more secure engagement between needle hub 216/216A and internal seal 226.

In some embodiments, external seal 220 is formed as an overmold of an elastomeric material on spike plate 224. In other embodiments, external seal 220 is secured to spike plate 224 in any suitable manner, for example by friction fit, suitable adhesives, or the like.

Any suitable material can be used for the manufacture of components of retractable blood collection device 200. Components that perform a sealing function such as needle seal 246, internal seal 226 and external seal 220 would typically be made from an elastomeric material, such as a thermoplastic elastomer. Components which must be rigid to support or rupture other components, such as needle hub 216, spike plate 224, or gripping arm 264 would typically be made of a relatively more rigid material such as polycarbonate, Styrolux™, polypropylene, or the like.

The correct positioning of needle support structure 218 axially within central body 204 of device 200 is assisted in the illustrated embodiment by a radially inwardly projecting internal wall 228. In some embodiments, internal wall 228 has a generally cylindrical configuration, so that it extends inside interior sidewall 222 around the entire circumference thereof. In some embodiments, internal wall 228 is discontinuous, for example, being formed as one or more discrete projections extending radially inwardly from interior sidewall 222. In some embodiments, when retractable blood collection device 200 is assembled, needle support structure 218 can be inserted proximally through the distal opening of central body 204 until the proximal edge of needle support structure 218 contacts internal wall 228. Internal wall 228 thus assists in positioning needle support structure 218 at the correct axial location within central body 204, and also prevents needle support structure 218 from being moved in the proximal direction, for example as might occur due to forces experienced when needle 214 is inserted into a subject.

Movement of needle hub 216 (and therefore needle 214) in the distal direction is prevented in the illustrated embodiment of FIGS. 13A, 15-17, and 19-21 through contact of the distal end of needle hub 216 with a proximally-extending neck 230 of needle assembly 208. Movement of needle hub 216A (and therefore needle 214) in the distal direction is prevented in the illustrated embodiment of FIGS. 13B, 14, 18A, 18B and 22 through contact of the distal end of needle hub 216A with inner wall 236A of needle assembly 208A.

A propellant chamber 232 is provided within a proximal portion of needle assembly 208 for containing a propellant to be used to retract needle 214. In the illustrated embodiment, propellant chamber 232 comprises a generally cylindrical channel 234 defined between an inner wall 236 and an outer wall 238 of the proximal end of needle assembly 208. A seal 240 extends over a mouth of channel 234 (i.e. between inner wall 236 and outer wall 238), to contain propellant therein.

In the illustrated embodiment, neck 230 extends axially from, and in the illustrated embodiment is integrally formed with, inner wall 236 of needle assembly 208. Propellant chamber 232 is thus initially spaced apart from needle support structure 218 in the distal direction.

Figure 15:
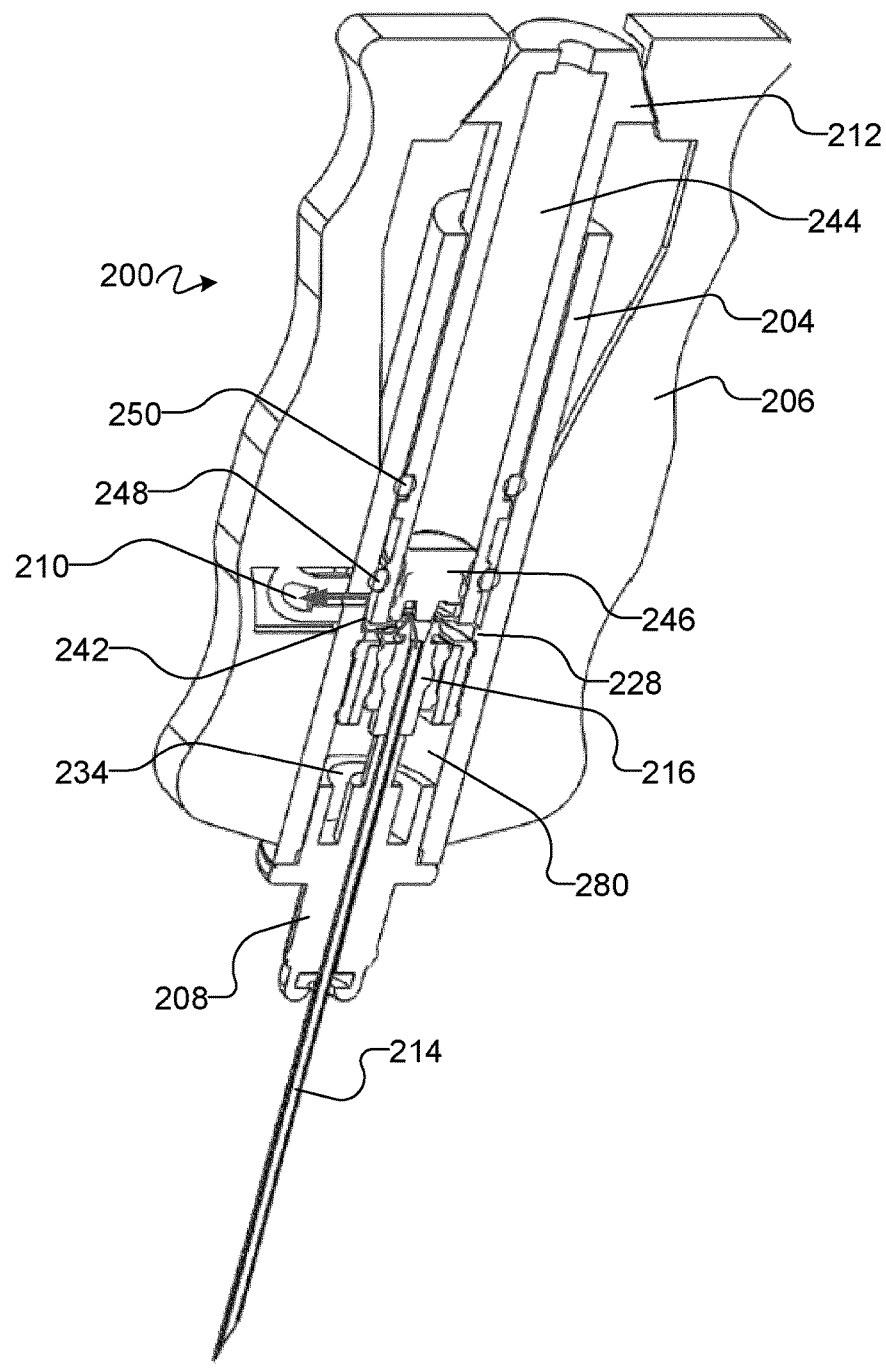
FIG. 15 shows a trimetric cross-sectional view of the example embodiment of Figure 12, with the seal of the propellant chamber removed for clarity.

With reference to FIG. 15, the path followed by blood as it is withdrawn from a subject through needle 214 and into blood collection tubing 210 is shown by arrow 242. Blood flows through needle 214 and out the proximal end of needle hub 216. A gap between the distal end of plunger 212 and internal wall 222 allows blood to flow between central body 204 and plunger 212, and the blood enters blood collection tubing 210 where the blood collection tubing 210 meets interior sidewall 222.

Plunger 212 has a retraction lumen 244 defined therein for receiving needle 214 when needle 214 is retracted. Blood is prevented from flowing into retraction lumen 244 by the sealing engagement of a needle seal 246 at the distal end of plunger 212. Needle seal 246 is engageable with needle hub 216 as described below to form a sealing engagement therewith to prevent further flow of blood through needle 214 after the desired sample(s) of blood has/have been collected.

Blood is also prevented from flowing in the proximal direction past plunger 212 by a distal blood tubing seal 248. A proximal blood tubing seal 250 is also provided around plunger 212 proximally of distal blood tubing seal 248, to prevent the flow of blood in the proximal direction past plunger 212 after retraction of needle 214 has been initiated. In the illustrated embodiment, both distal and proximal blood tubing seals 248, 250 are O-ring seals that encircle and sealingly engage recesses formed on plunger 212 at appropriate axial locations, and sealingly engage interior sidewall 222. However, any suitable seal could be used to provide distal and proximal blood tubing seals 248, 250, and it is not necessary that the same type of seal be used for each of seals 248 and 250. In some embodiments, either or both of blood tubing seals 248, 250 could be formed as an overmold on plunger 212.

In use, a user begins with a fully assembled retractable blood collection device 200, and couples blood collection tubing 210 to any suitable blood collection reservoir. A user would also take any steps necessary to prepare the device to which retractable blood collection device 200 is connected for use. A user then removes any cap or protective covering from needle 214, inserts needle 214 into the subject from whom blood is to be drawn, and allows the flow of blood to the desired blood collection reservoir to begin. In some embodiments, the blood collection reservoir is an evacuated container, to assist in drawing blood from the subject. In some embodiments, the natural flow of blood from the subject is used to fill the blood collection reservoir.

After the desired blood sample(s) have been collected from the subject, a user may take any steps necessary to terminate the flow of blood into the chosen blood collection reservoir through blood collection tubing 210. For example, in the case of an evacuated collection reservoir such as a Vacutainer™, the operator can remove the Vacutainer™ from the collection device so that the collection device is sealed, for example by a sheath similar to proximal needle seal 84 described above provided on a cannula extending between blood collection tubing 210 and the Vacutainer™. A user can then either initiate retraction of needle 214 as described below while needle 214 is still in the subject (subject to regulatory requirements), or withdraw needle 214 from the subject and initiate retraction. Alternatively, and subject to regulatory requirements, after the Vacutainer™ has been filled with blood, retraction of needle 214 can be initiated while needle 214 is still in the subject, and then a user can deal with further processing of the filled Vacutainer™.

Figure 16:
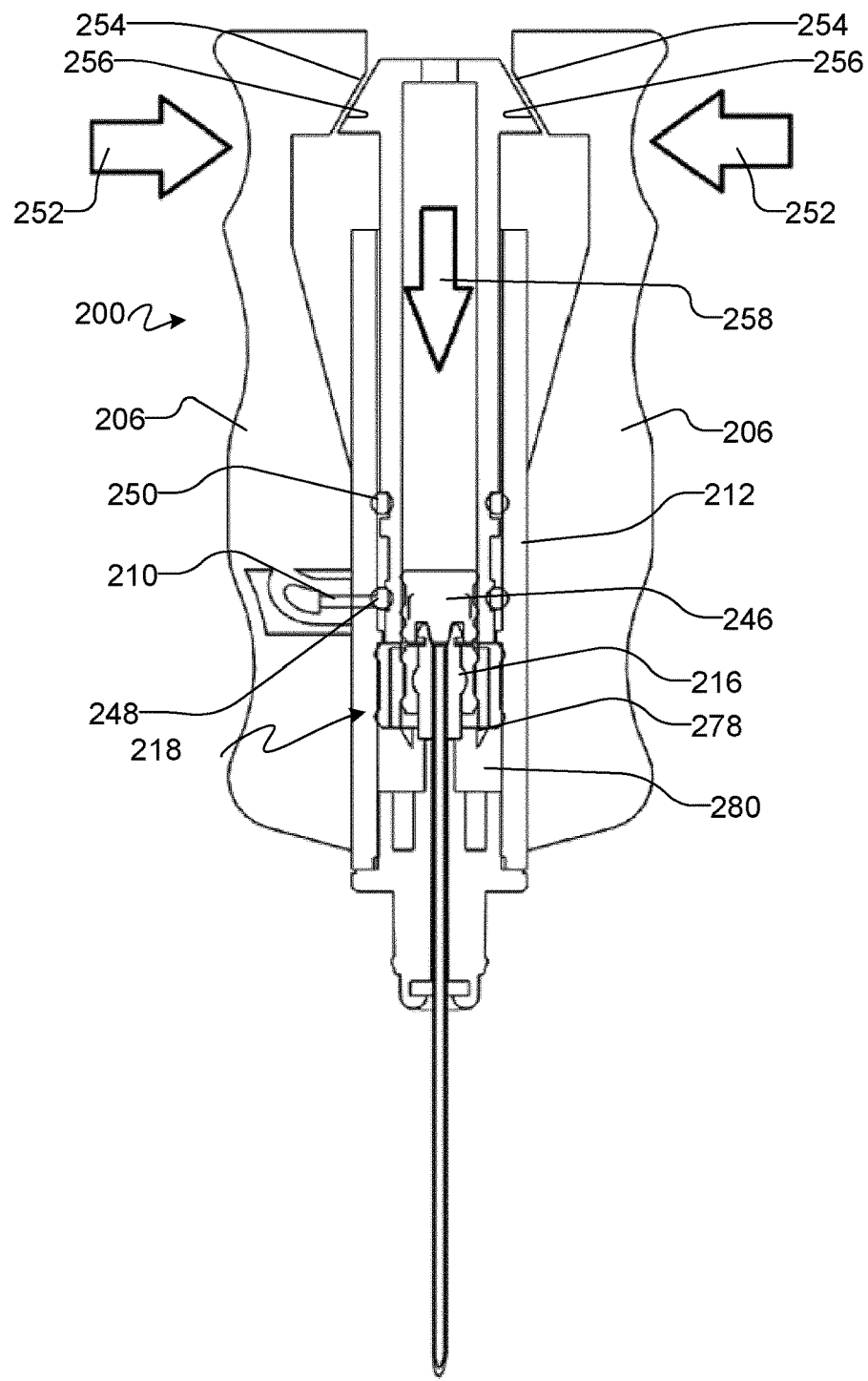
FIG. 16 shows a cross-sectional view of the example embodiment of FIG. 12 at the first activation step.

With reference to FIG. 16, a user initiates the retraction process and, if blood flow has not already been terminated, terminates the flow of blood through blood collection tubing 210, by pressing wings 206 radially inwardly towards one another, as indicated by arrows 252. This causes angled surfaces 254 on the proximal portion of wings 206 to press radially inwardly and distally against corresponding angled surfaces 256 provided at the proximal end of plunger 212. Angled surfaces 254 are angled outwardly in the distal direction, and angled surfaces 256 are also angled outwardly in the distal direction in a complementary fashion, so that the force applied by angled surfaces 254 against angled surfaces 256 causes plunger 212 to move axially in the distal direction, as indicated by arrow 258.

Distal movement of plunger 212 causes distal blood tubing seal 248 to slide distally past the inlet of blood collection tubing 210 in interior sidewall 222. This seals the blood flow path indicated by arrow 242, preventing further flow of blood into or out of blood collection tubing 210. Proximal blood tubing seal 250 prevents the flow of blood in the proximal direction past plunger 212.

Distal movement of plunger 212 also causes needle seal 246 to become sealingly engaged with a first portion of the needle support structure 218, which is needle hub 216 in the illustrated embodiment. This step of forming a sealed engagement between needle seal 246 and needle hub 216 is referred to herein as the first activation step.

Figure 17:
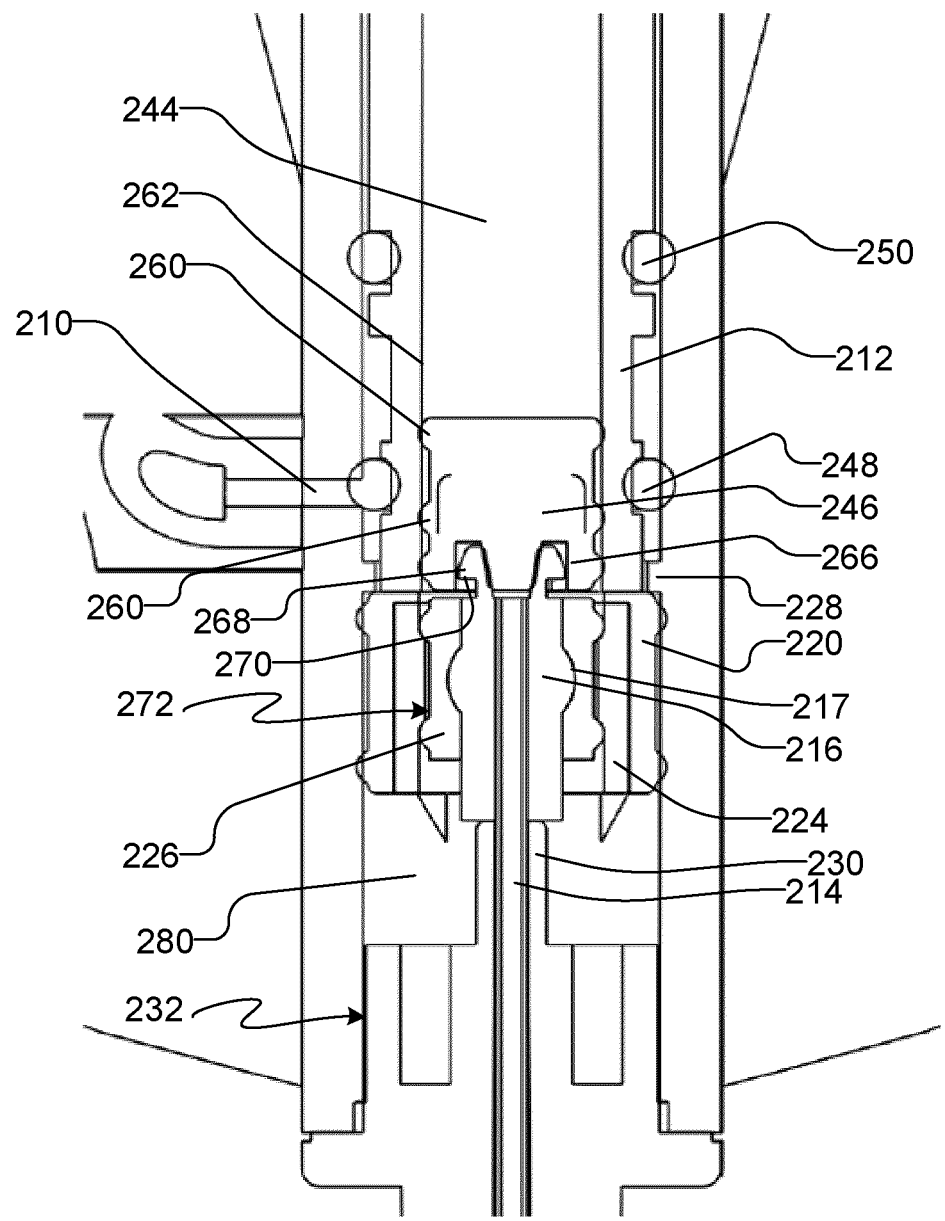
FIG. 17 shows a partial enlarged cross-sectional view of components of the needle retraction assembly of the example embodiment of FIG. 12 at the first activation step.
Figure 18A:
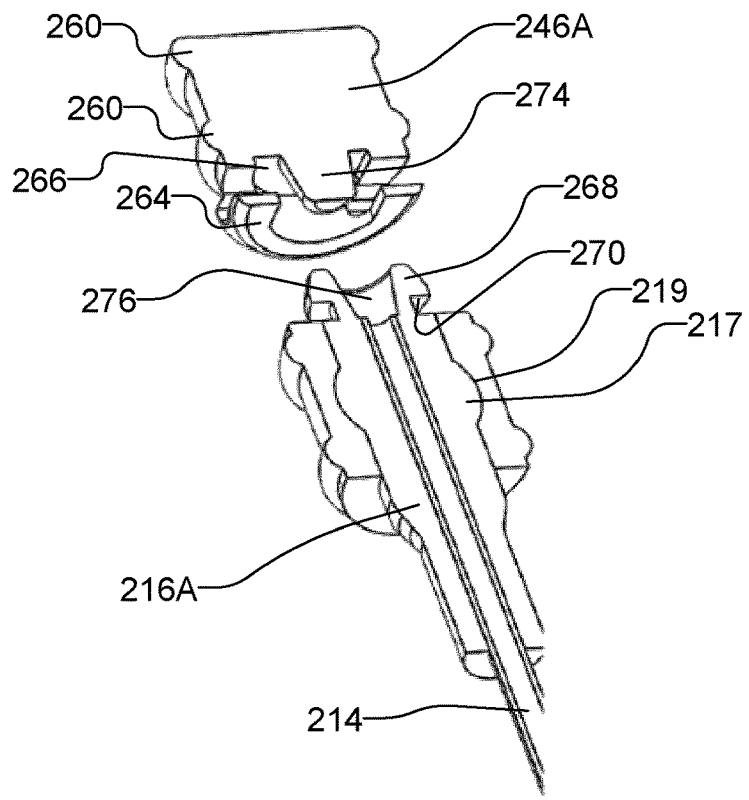
FIG. 18A shows a partial enlarged cross-sectional view of the components of the needle retraction assembly of the embodiment illustrated in FIG. 13B in their separated configuration.
Figure 18B:
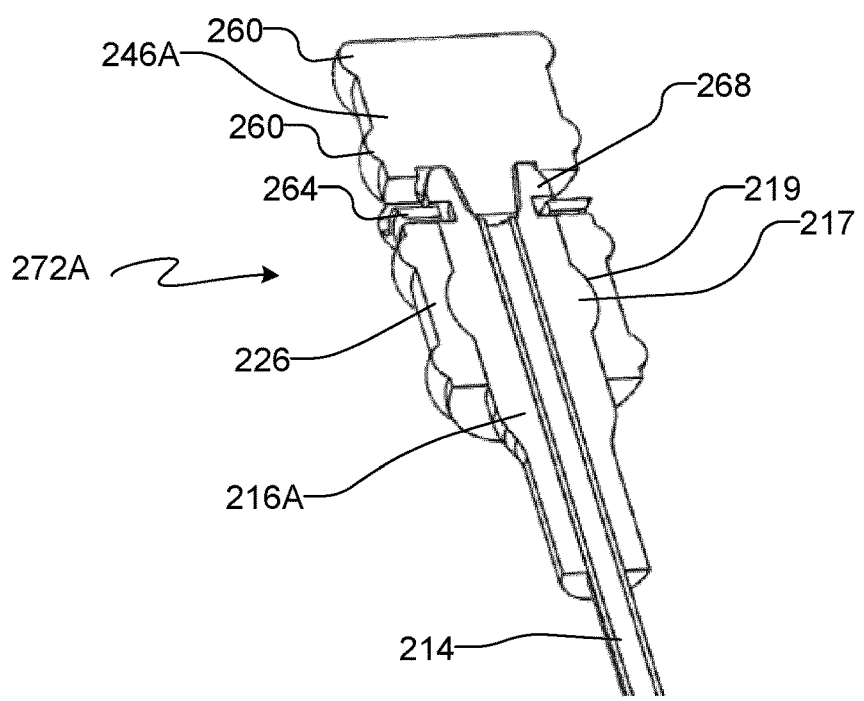
FIG. 18B shows a partial enlarged cross-sectional view of these components in their engaged configuration.

The features of needle seal 246/246A and needle hub 216/216A in the illustrated embodiment are shown in more detail in FIGS. 17, 18A and 18B. Needle seal 246/246A has features 260 that slideably and sealingly engage the inner surface 262 of retraction lumen 244. In the illustrated embodiment, these features comprise two or three generally circular ribs extending radially outwardly from the periphery of needle seal 246/246A. Providing more than one rib may help to maintain a consistent orientation of needle seal 240 within retraction lumen 244. However, any desired number and arrangement of sealing features 260 that allows for slideable sealing engagement with inner surface 262 could be used.

Needle seal 246/246A also includes a feature for securing needle seal 246/246A to needle hub 216/216A to form retraction assembly 272/272A. In the illustrated embodiment, this feature comprises a gripping arm 264 (FIGS. 18A and 18B) that extends radially inwardly from the distal edge of a receptacle 266 provided in the distal portion of needle seal 246/246A.

Figure 13B:
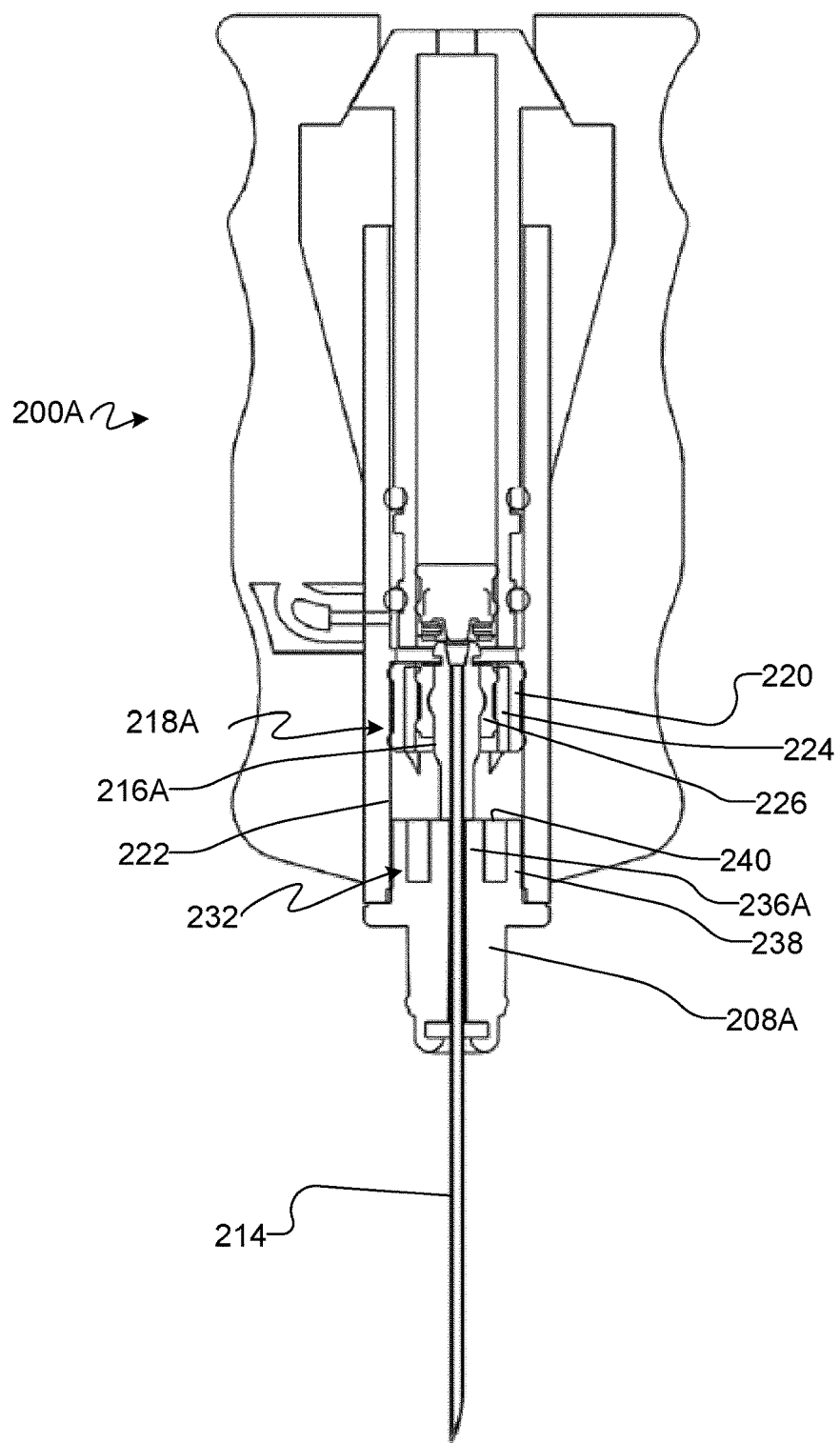
FIG. 13B shows a cross-sectional view of a second example embodiment of a retractable blood collection device that is generally similar to the embodiment of FIG. 12.
Figure 14:
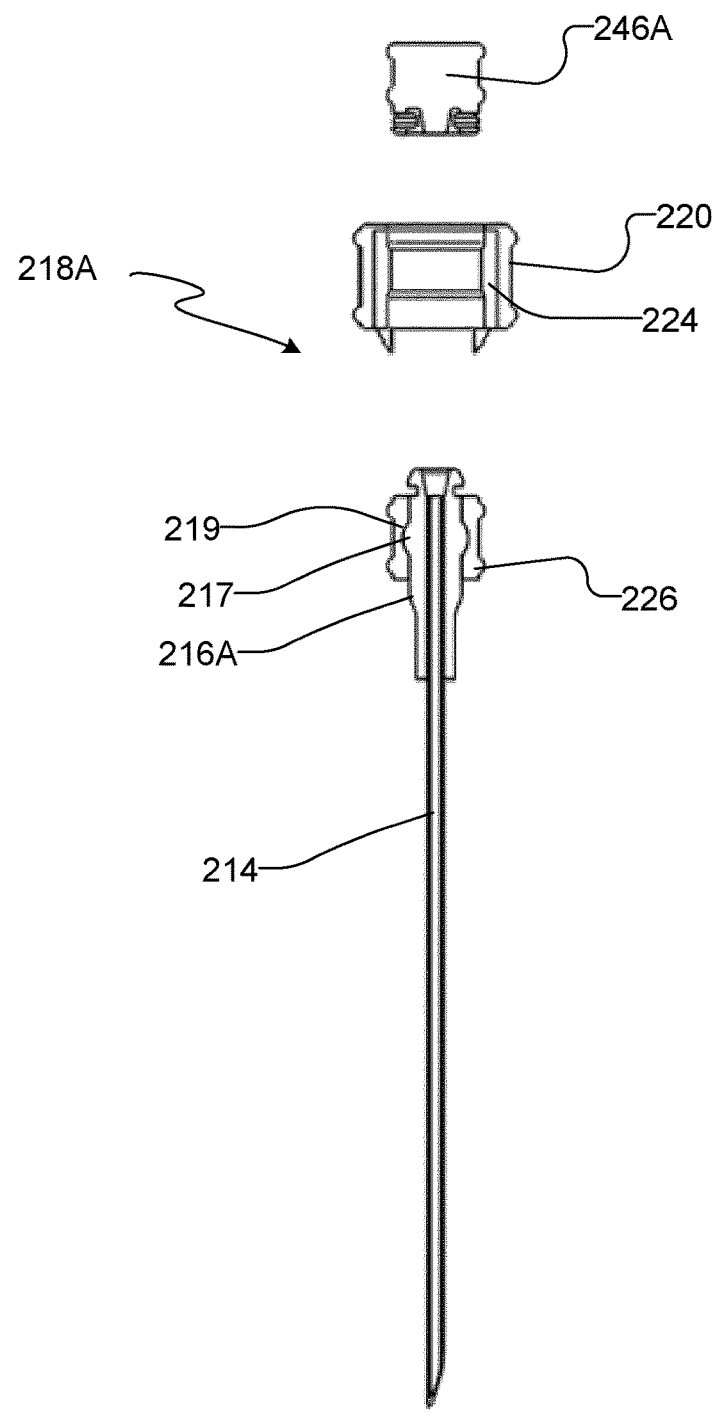
FIG. 14 shows an exploded view of components of the needle support structure and the needle seal in the example embodiment of FIG. 13B.

Receptacle 266 is sized and configured to receive the proximal tip 268 of needle hub 216/216A. Proximal tip 268 has a locking edge 270 on the distal edge thereof, which engages in a snap fit with gripping arm 264 during the first activation step. This snap fit secures needle seal 246/246A to needle hub 216/216A (and therefore to internal seal 226 and needle 214, which are secured to needle hub 216/216A) to form needle retraction assembly 272/272A. Movement of needle hub 216 in the distal direction is prevented by virtue of the contact of needle hub 216 with neck 230 of needle assembly 208. Movement of needle hub 216A in the distal direction is prevented by virtue of the contact of the distal end of needle hub 216A with inner wall 236A of needle assembly 208A (FIG. 13B).

Figure 20:
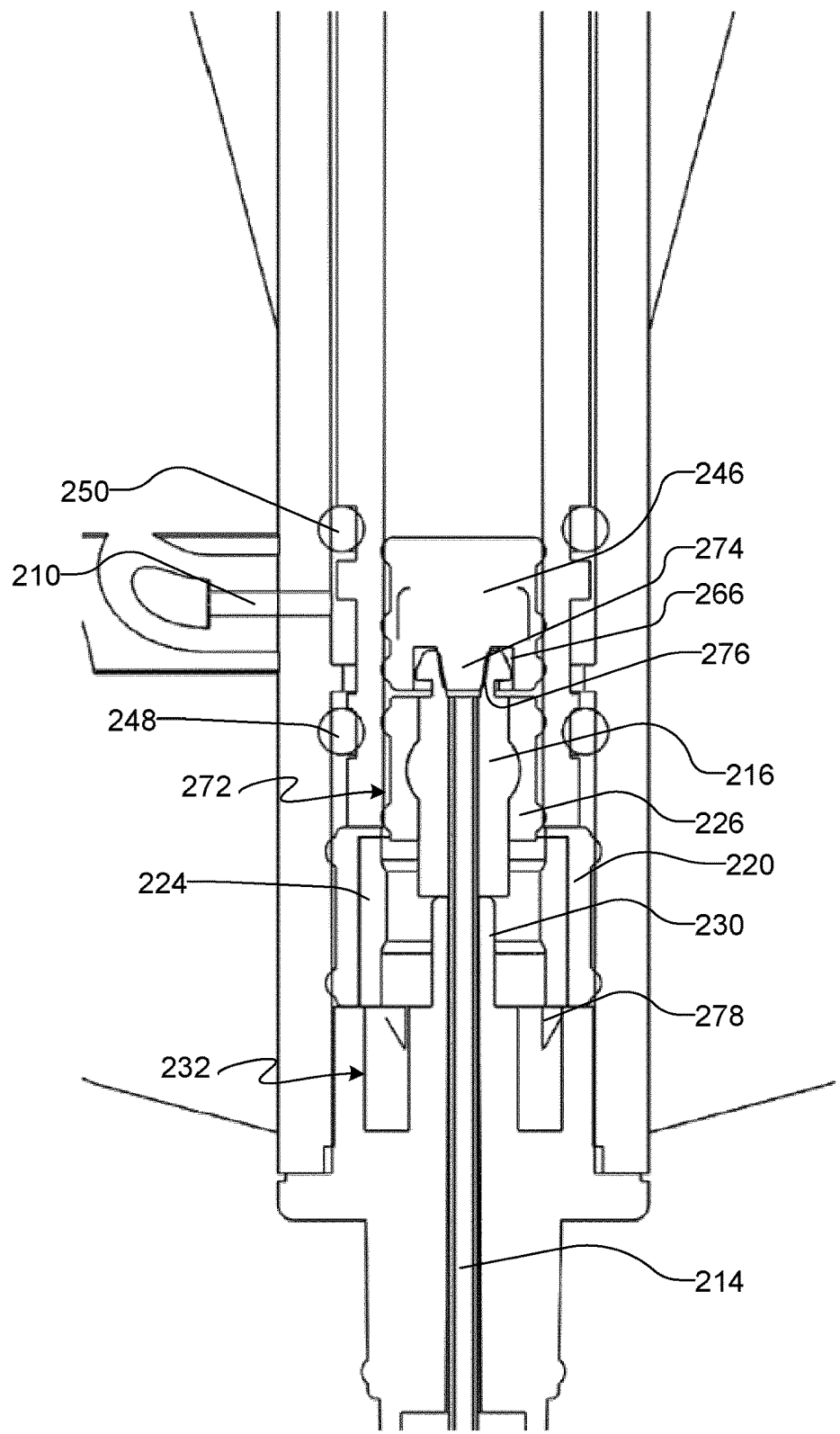
FIG. 20 shows a partial enlarged cross-sectional view of components of the needle retraction assembly of the example embodiment of FIG. 12 at the second activation step.

With reference to the embodiment illustrated in FIG. 20, a sealing engagement is provided between needle seal 246 and needle hub 216 during the first activation step. In the illustrated embodiment, the sealing engagement is provided by the engagement of a central projection 274 extending in the distal direction within receptacle 266 with a correspondingly shaped aperture 276 provided at the proximal end of needle hub 216. In the illustrated embodiment, central projection 274 has a sealing surface that tapers radially inwardly in the distal direction, and central projection 274 is received in a correspondingly tapered sealing surface provided in aperture 276, which also tapers radially inwardly in the distal direction. Needle seal 246A and needle hub 216A are similarly provided with a central projection 274 and aperture 276, respectively, as illustrated in FIGS. 18A and 18B.

Figure 19:
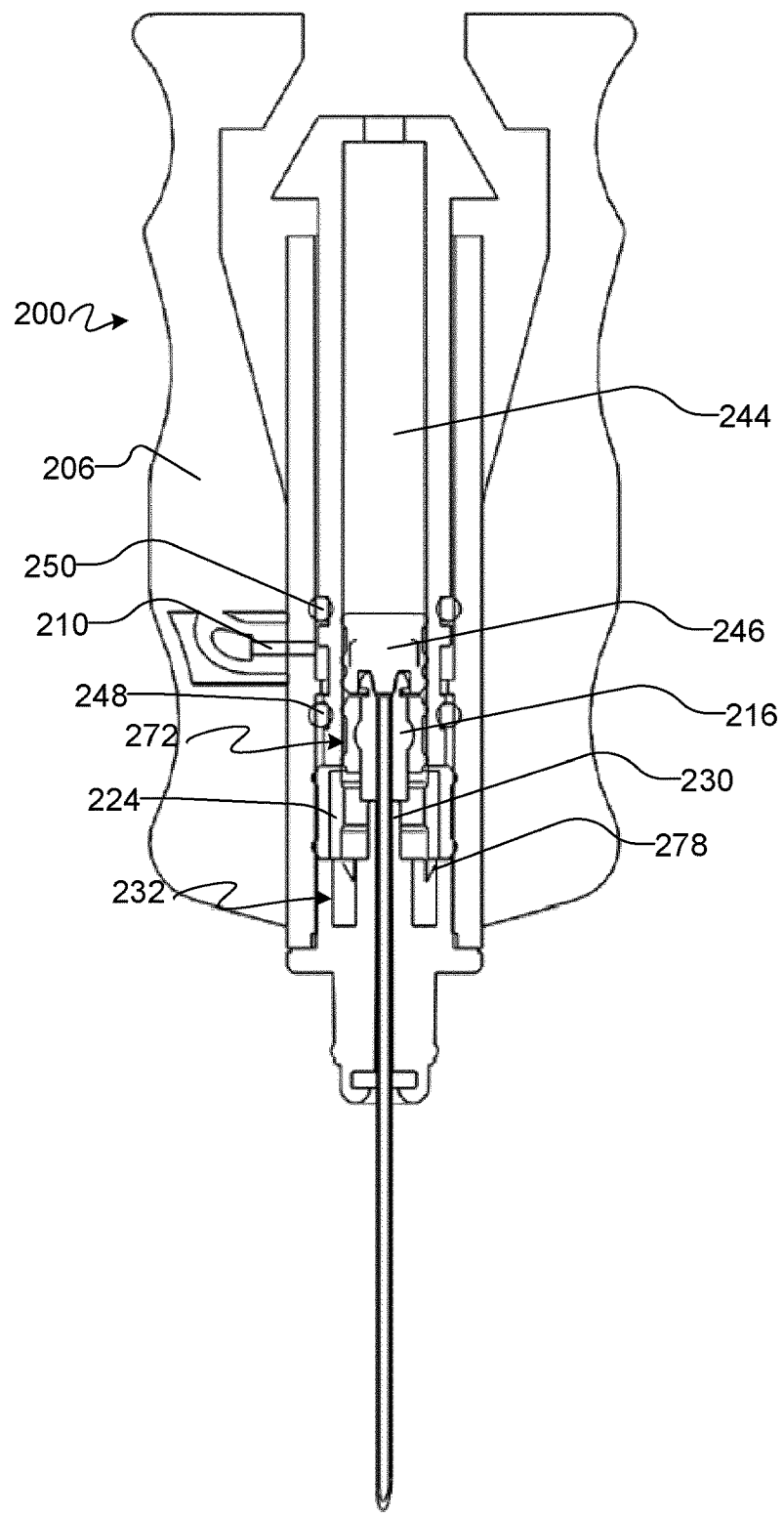
FIG. 19 shows a cross-sectional view of the example embodiment of FIG. 12 at the second activation step.

With reference to FIGS. 19 and 20, continued application of force against wings 206 in the direction of arrows 252 by a user advances plunger 212 farther in the distal direction after needle seal 246 and needle hub 216 have become sealingly engaged. This distal movement of plunger 212 advances spikes 278 that project distally from spike plate 224 towards propellant chamber 232, ultimately resulting in the rupture of seal 240 to release propellant within a propellant release chamber 280 defined between propellant release chamber 232, the interior sidewall 222 of central body 204, and the needle retraction assembly 272.

Distal movement of needle retraction assembly 272 (needle hub 216, internal seal 226, needle 214 and needle seal 246 in the illustrated embodiment) as plunger 212 advances is prevented in the illustrated embodiment by contact between needle hub 216 and neck 230 (or needle hub 216A and inner wall 236A in the embodiment of FIG. 13B), so that a first portion of the needle support structure 218 remains engaged with needle seal 246. However, spike plate 224 and external seal 220 (a second portion of the needle support structure 218) continue to move in the distal direction together with plunger 212, and are separated from internal seal 226.

While in the illustrated embodiment, the needle retraction assembly 272 has been described as including needle hub 216, internal seal 226, needle 214 and needle seal 246, in alternative embodiments, the needle retraction assembly 272 does not include internal seal 226. For example, in some embodiments, internal seal 226, external seal 220, and spike plate 224 could be integrally formed as a single piece, or as only two components (i.e. a rigid component bearing spikes 278 and a relatively more flexible or elastomeric component that seals against both needle hub 216 and the interior sidewall 222 of central body 204, so that just needle hub 216 is released from this relatively more flexible elastomeric component for retraction as part of needle retraction assembly 272). In some such embodiments, the shaping of needle hub 216 is modified to provide a stronger engagement between needle hub 216 and the relatively more flexible elastic component, to minimize the risk that needle hub 216 may become dislodged from the elastic component before retraction is initiated. For example, in some embodiments, the central bulge 217 of needle hub 216 can be provided with an O-ring seal and two tapered seals, similar to first and second radial sealing features 42, 44 described above. In some embodiments in which internal seal 226 is used, the risk of failure of retraction due to a failure of the needle seal 246 becoming fully engaged with needle hub 216 is lessened, since seal 226 reduces the risk that a flow path for propellant could be created around needle hub 216.

Figure 21:
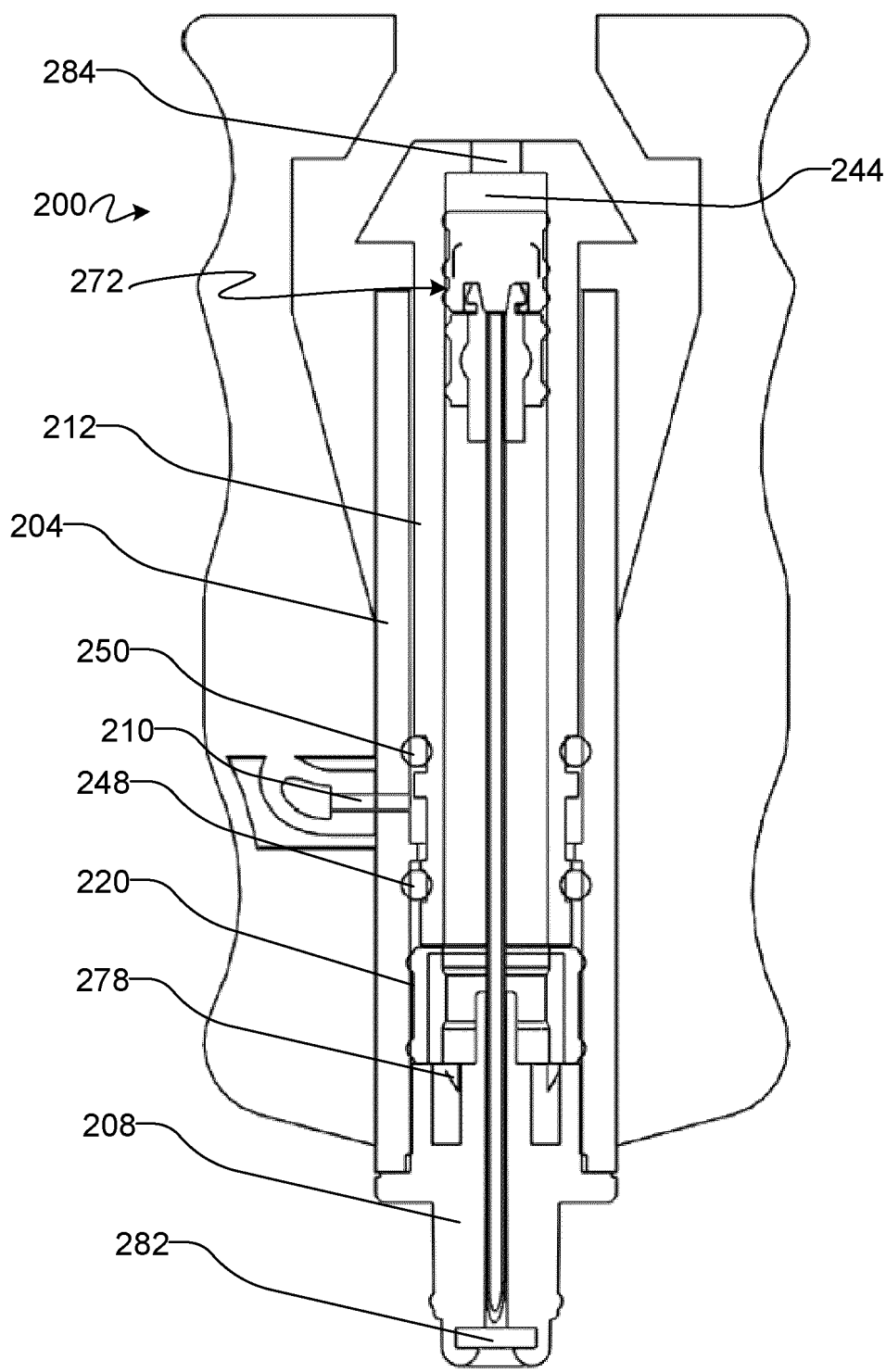
FIG. 21 shows a cross-sectional view of the example embodiment of FIG. 12 with the needle retracted.

Ultimately, spikes 278 contact and rupture seal 240, releasing propellant into propellant release chamber 280 and driving needle retraction assembly 272 proximally within retraction lumen 244 in a third activation step. The needle retraction assembly 272 ultimately comes to rest within retraction lumen 244, as illustrated in FIG. 21 in its final retracted position. An aperture 284 is provided through the proximal end of plunger 212, so that air within retraction lumen 244 is vented to the external atmosphere during proximal movement of needle retraction assembly 272. Aperture 284 could be positioned within plunger 212 at any location proximal of the final resting point of needle retraction assembly 272.

Figure 22:
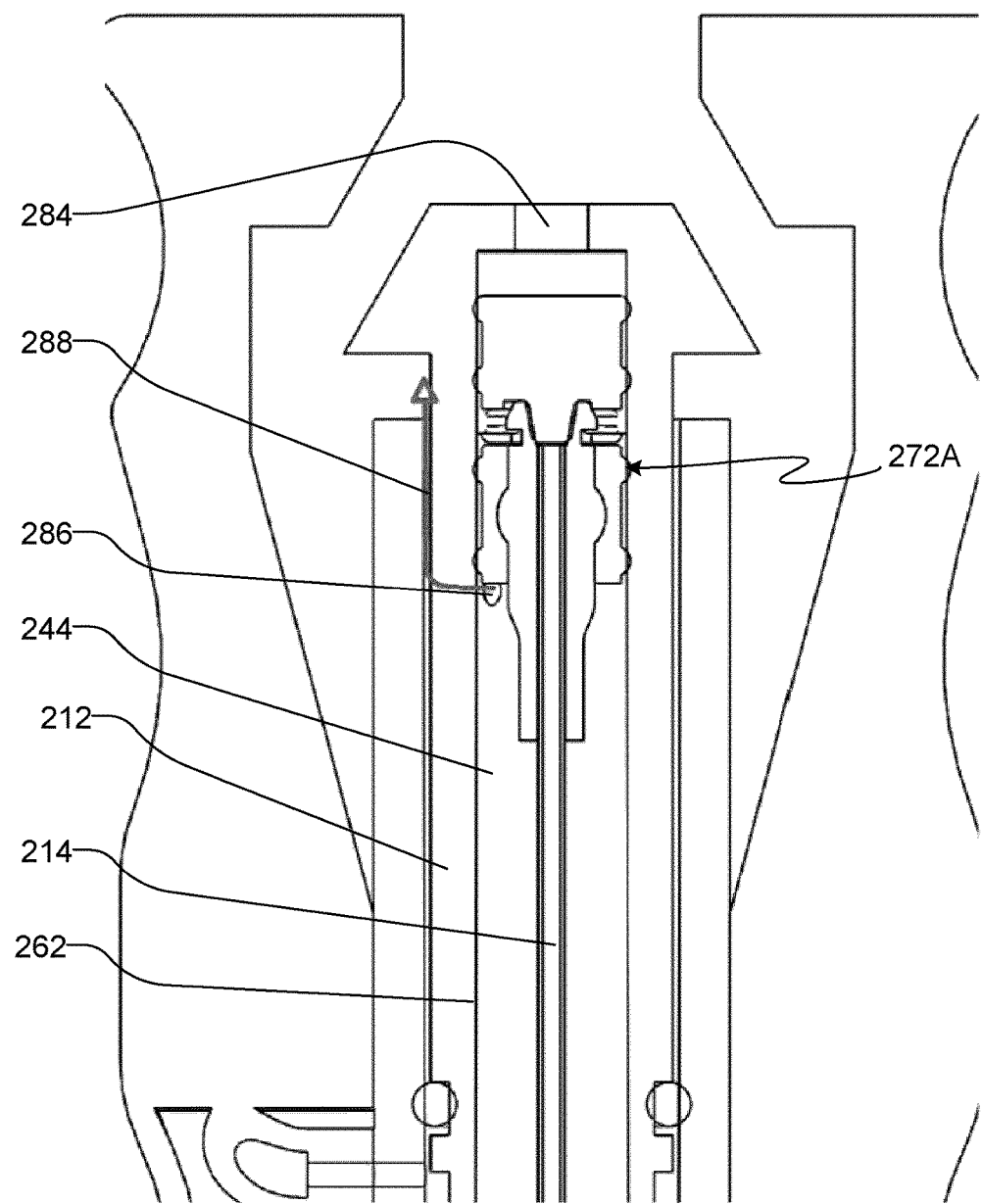
FIG. 22 shows a partial enlarged cross-sectional view of the example embodiment of FIG. 13B that includes a vent hole in the plunger to vent excess propellant to the atmosphere after needle retraction is complete.
Figure 23A:
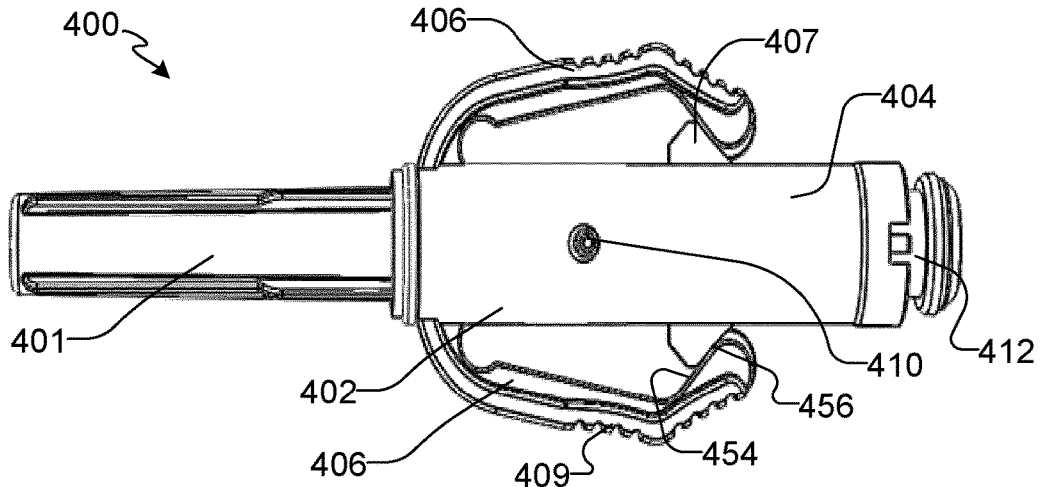
FIG. 23A is a side view of a further example embodiment of a blood collection device.
Figure 23B:
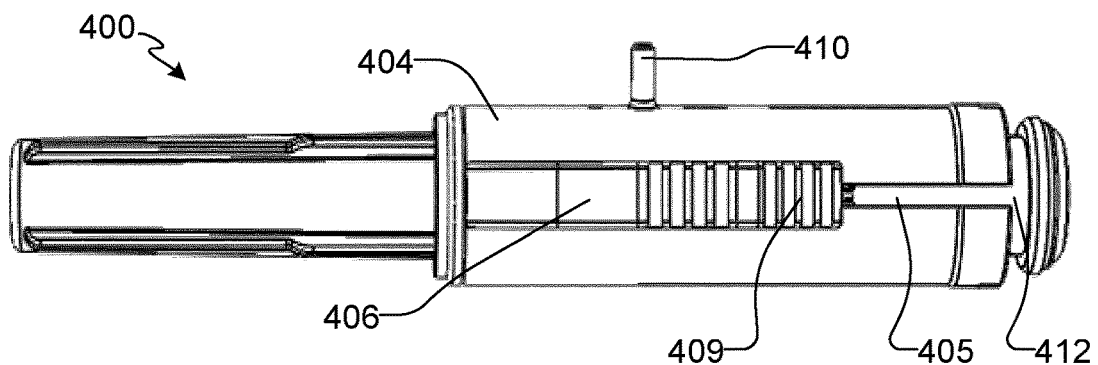
FIG. 23B is a side view thereof rotated by 90°.

With reference to FIG. 22, in some embodiments, an aperture 286 is provided through the wall of plunger 212 to allow the release of any excess propellant remaining after the needle retraction assembly 272A has reached its final position. Aperture 286 is positioned just distally of the final resting position of needle retraction assembly 272A, so that the propellant will be able to propel retraction assembly 272A in the proximal direction until retraction assembly 272A (not including needle 214, which is not in sealing engagement with the inner surface 262 of retraction lumen 244) moves proximally of aperture 286. At that point, remaining propellant can exit retraction lumen 244 via aperture 286, and flow to the external atmosphere via the gap between plunger 212 and central body 204, as indicated by arrow 288.

In some embodiments, as best seen in FIG. 21, a distal needle seal 282 is provided near the distal portion of needle assembly 208. In the illustrated embodiment, distal needle seal 282 is secured at the distal end of needle assembly 208. Distal needle seal 282 is made from a soft material to sealingly engage around the outside surface of needle 214 and prevent the flow of propellant past needle 214 and out of the propellant release chamber 280. The material from which distal needle seal 282 is made is selected to provide an airtight seal after needle 214 has passed through distal needle seal 282 during retraction.

In the illustrated embodiment, retraction lumen 244 is generally cylindrical in shape, as are the other components of retractable blood collection device 200, and retraction lumen 244 has a generally circular cross-section. While a cylindrical shape is the conventional shape for blood collection devices, other shapes could be used (e.g. a generally triangular or square cross-section), so long as all components are modified accordingly and such shapes allow the relative release and sliding movement of components of blood collection device 200 as described above.

With reference to FIGS. 23A, 23B and 24-29, an alternative embodiment of a retractable blood collection device 400 is illustrated. Retractable blood collection device 400 is generally similar to retractable blood collection device 200, and elements of blood collection device 400 that perform the same function as elements of blood collection device 200 are illustrated with reference numerals incremented by 200. In the illustrated embodiment, a cap 401 is provided to cover needle 414 prior to use.

Retractable blood collection device 400 differs from retractable blood collection device 200 by having a pair of opposed longitudinally extending slots 405 (FIG. 23B) formed at the proximal end of central body 404. Angled surfaces 456 of plunger 412 are provided on radially outwardly extending projections 407 formed on plunger 412 that extend through slots 405, rather than at a distal end of the plunger as for plunger 212. Plunger 412 is moveable within central body 404 so that projections 407 slide longitudinally in the distal direction within slots 405 when a user actuates the retraction mechanism by pressing wings 406 radially inwardly. In the illustrated embodiment, the outer edges of wings 406 are provided with ridged contact surfaces 409, to facilitate a user securely grasping and pressing wings 406 radially inwardly. In alternative embodiments, ridged contact surfaces 409 are omitted. In some embodiments, the use of slots 405 and projections 407 allows for retractable blood collection device 400 to be mad of a smaller size than a corresponding retractable blood collection device 200.

Figure 24:
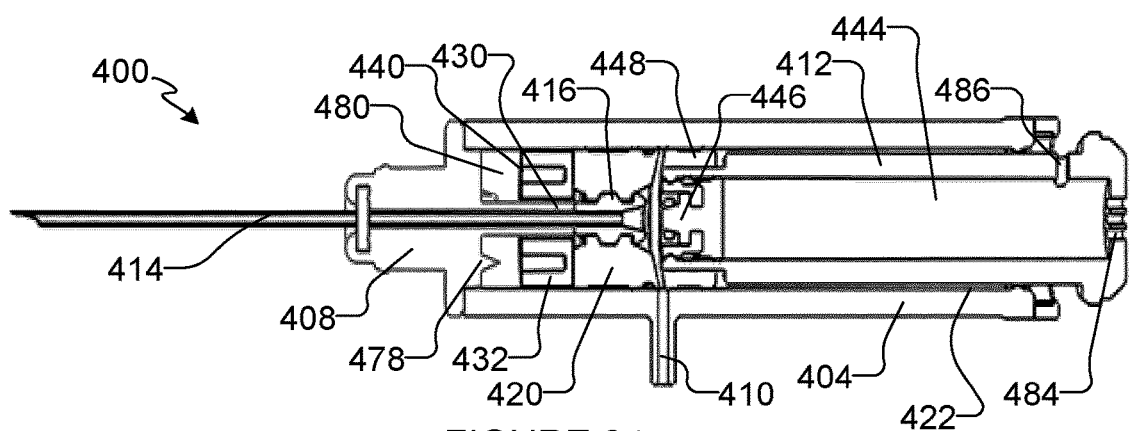
FIG. 24 is a sectional view of the embodiment illustrated in FIGS. 23A and 23B, with the device in an initial, unactivated configuration, ready to draw blood from a subject, in which the wings are not visible.
Figure 25:
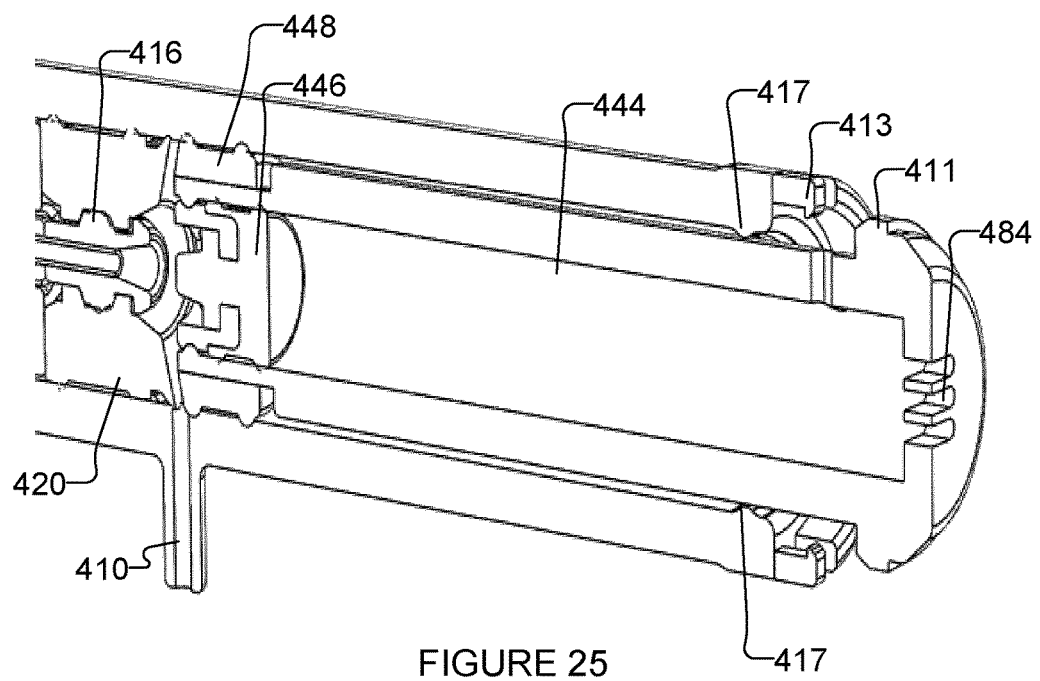
FIG. 25 is an enlarged partial sectional view of the embodiment shown in FIG. 24 in the initial, unactivated configuration, in which the wings are not visible.

With reference to FIGS. 24 and 25, retractable blood collection device 400 also does not have a spike plate similar to spike plate 224. Spikes 478 are provided at the distal end of propellant release chamber 480, and propellant release chamber 432 is initially secured within propellant release chamber 480 proximally of spikes 478. In alternative embodiments, spikes 478 could be instead provided extending distally from seal 420 and propellant chamber 432 could be initially positioned distally of the spikes, so that movement of plunger 412 in the distal direction would cause the spikes to impinge upon and rupture the propellant chamber.

Needle hub 416 is secured in place via a single seal 420, which is also in sealing engagement with the inside surface 422 of central body 404. Needle hub 416 is restrained against movement in the distal direction upon the application of a post-injection force by the engagement of the distal end of needle hub 416 with a proximally extending neck 430 of needle assembly 408.

Seal 420 is frictionally but slideably engaged with the inside surface of central body 404, so that when a user actuates the retraction mechanism by pressing wings 406 radially inwardly to move plunger 412 in the distal direction, this causes seal 420 to slide distally within propellant release chamber 480. Distal movement of seal 420 also causes distal movement of propellant release chamber 432, so that seal 440 of propellant release chamber 432 impinges on spikes 478 and is ruptured, thereby releasing propellant into propellant release chamber 480. In some embodiments, propellant release chamber 432 is provided as an overmold to seal 420. In some embodiments, propellant release chamber 432 is provided as a separate component, for example as a gas release cell as described in PCT Publication WO 2015/145207, which is incorporated by reference herein.

The distal tip of plunger 412 is provided with a needle seal 446, which can engage with needle hub 416 as described above for needle seal 246 and needle hub 216 to form a needle retraction assembly 472 comprising the needle seal 446, needle hub 416, and needle 414.

Figure 27:
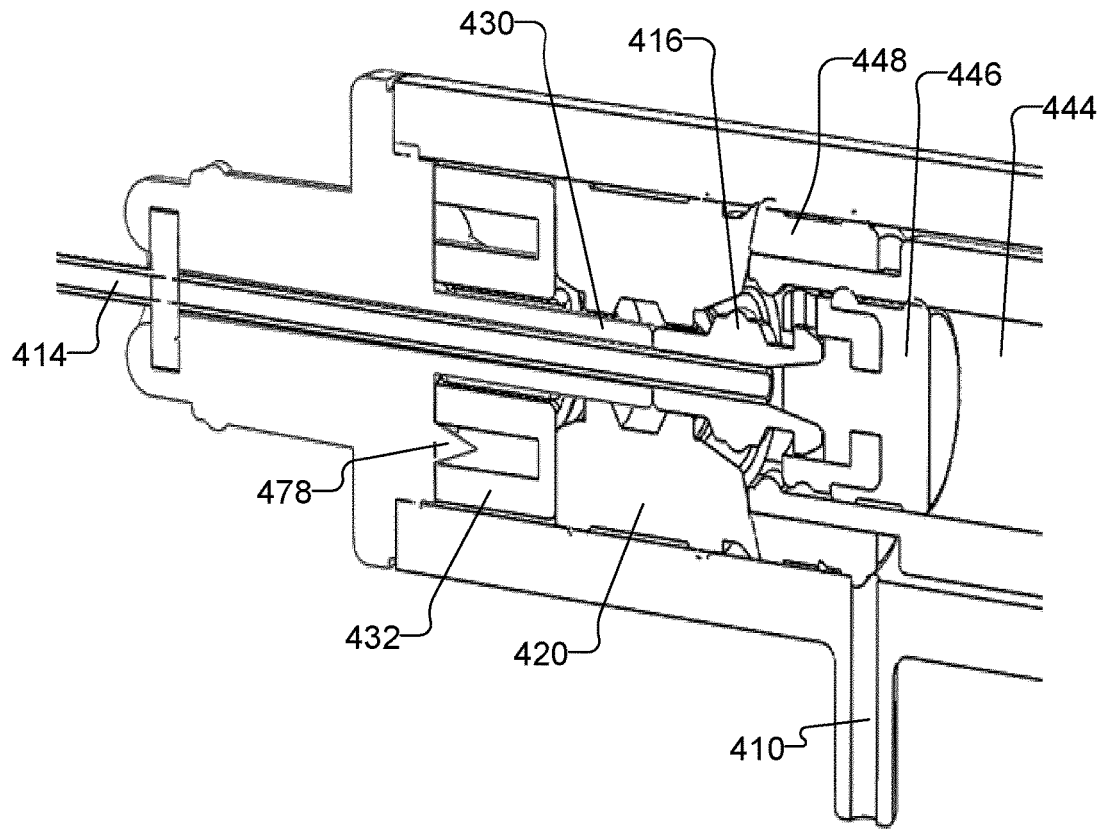
FIG. 27 is an enlarged partial sectional view of the embodiment illustrated in FIG. 26 after a user has initiated the retraction mechanism, in which the wings are not visible.

A fluid flow path to allow the flow of blood through needle 414 and into blood collection tubing 410 is provided when retractable blood collection device 400 is in its initial, unactivated configuration. Blood can flow through needle 414, through the proximal end of needle hub 416, past the tip of plunger 412 (with needle seal 446 preventing blood from entering retraction lumen 444) and out through blood collection tubing 410. A single plunger seal 448 is provided at the distal end of plunger 412, and is in sealing engagement with interior sidewall 422 of central body 404. Plunger seal 448 is positioned to allow blood to flow into blood collection tubing 410, but to prevent the flow of blood proximally past plunger 412. When a user actuates the retraction mechanism of retractable blood collection device 400 by pressing wings 406 radially inwardly, so that angled sliding surfaces 454, 456 slide relative to one another to move plunger 412 in the distal direction, plunger seal 448 slides over and sealingly covers the entry to blood collection tubing 410 to prevent the further flow of blood therethrough, as shown in FIG. 27. In alternative embodiments, two blood tubing seals similar to distal blood tubing seal 248 and proximal blood tubing seal 250 could be provided at the distal end of plunger 412 in place of plunger seal 448.

In the illustrated embodiment, an internal ridge 417 is provided on inner surface 422 of central body 404. Internal ridge 417 projects radially inwardly from inner surface 422 to minimize side-to-side motion of plunger 412, to minimize interference of moving parts when the retraction mechanism is actuated. In the illustrated embodiment, internal ridge 417 is provided near the proximal end of central body 404. In alternative embodiments, the position of internal ridge 417 could be varied, or internal ridge 417 could be omitted.

Figure 26:
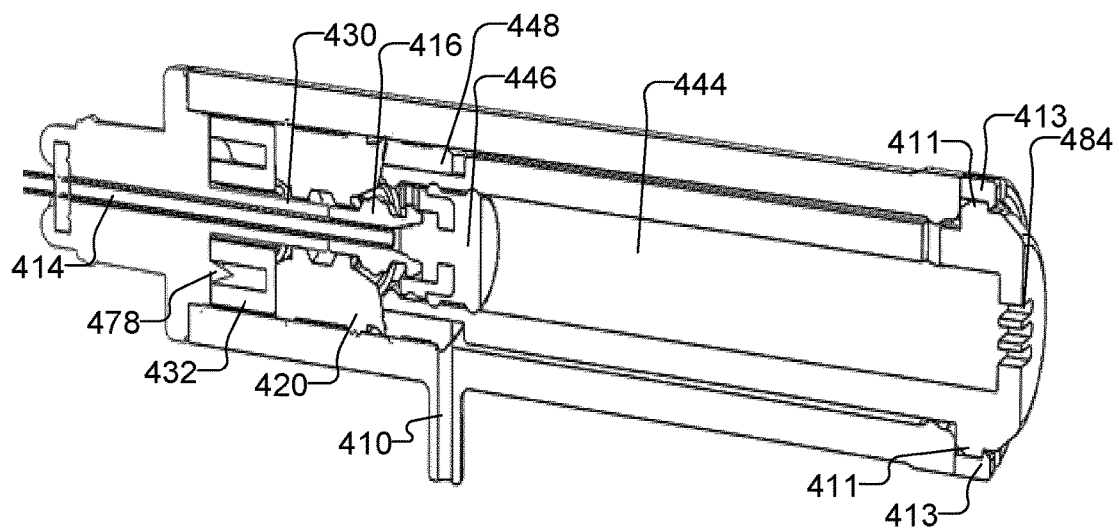
FIG. 26 is a sectional view of the embodiment illustrated in FIG. 24, after a user has initiated activation of the needle retraction mechanism, in which the wings are not visible.

With reference to FIG. 26, after a user actuates the retraction mechanism of retractable blood collection device 400 by pressing wings 406 radially inwardly, needle seal 446 sealingly engages needle hub 416 with a snap-fit engagement, as described above for needle seal 246 and needle hub 216, to form needle retraction assembly 472. Distal movement of seal 420 also displaces needle hub 416 from seal 420 and causes propellant chamber 432 to move distally and impinge upon spikes 478, to release propellant from propellant chamber 432 and cause retraction of needle retraction assembly 472 into retraction lumen 444.

In the illustrated embodiment, retractable blood collection device 400 is provided with a locking mechanism, to lock plunger 412 in place after use of the device. In the illustrated embodiment, the locking mechanism comprises a pair of snap-fit engagement members 411, 413. A snap fit member 411 is provided at the distal portion of plunger 412 that is slideable in the distal direction past a corresponding snap fit member 413 provided at the distal portion of central body 404. Snap fit members 411, 413 are configured to prevent relative movement of plunger 412 in the proximal direction after snap fit members 411, 413 have been engaged. In the illustrated embodiment, each of snap fit members 411, 413 is provided with a generally flat radially extending surface, so that after snap fit member 411 moves past snap fit member 413, the generally flat radially extending surfaces come into contact, thereby preventing movement of plunger 412 in the proximal direction. This prevents re-use of retractable blood collection device 400.

Figure 28:
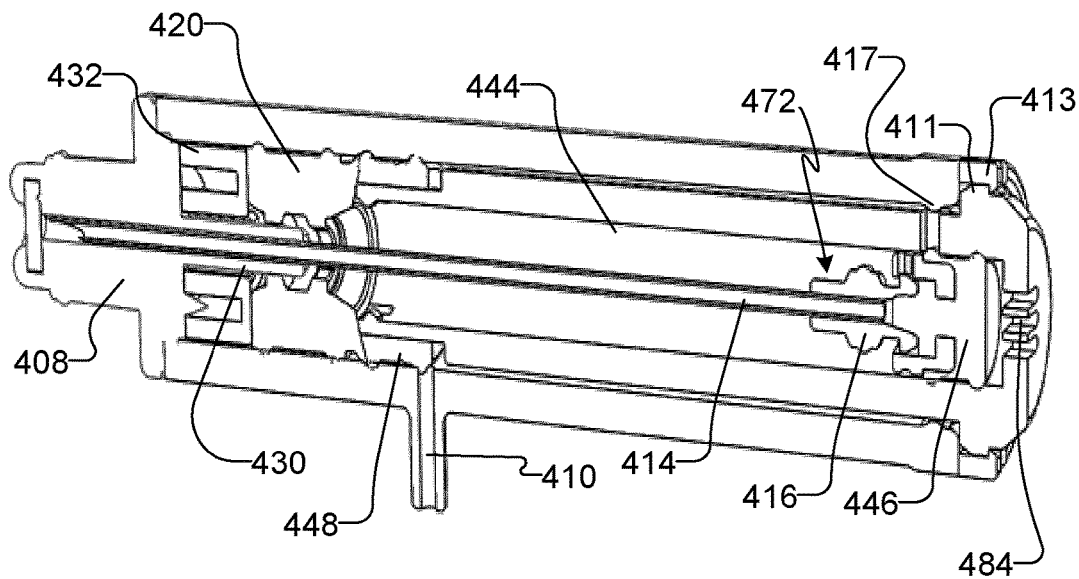
FIG. 28 is a sectional view of the embodiment illustrated in FIGS. 23A-27 after the needle has been retracted.
Figure 29:
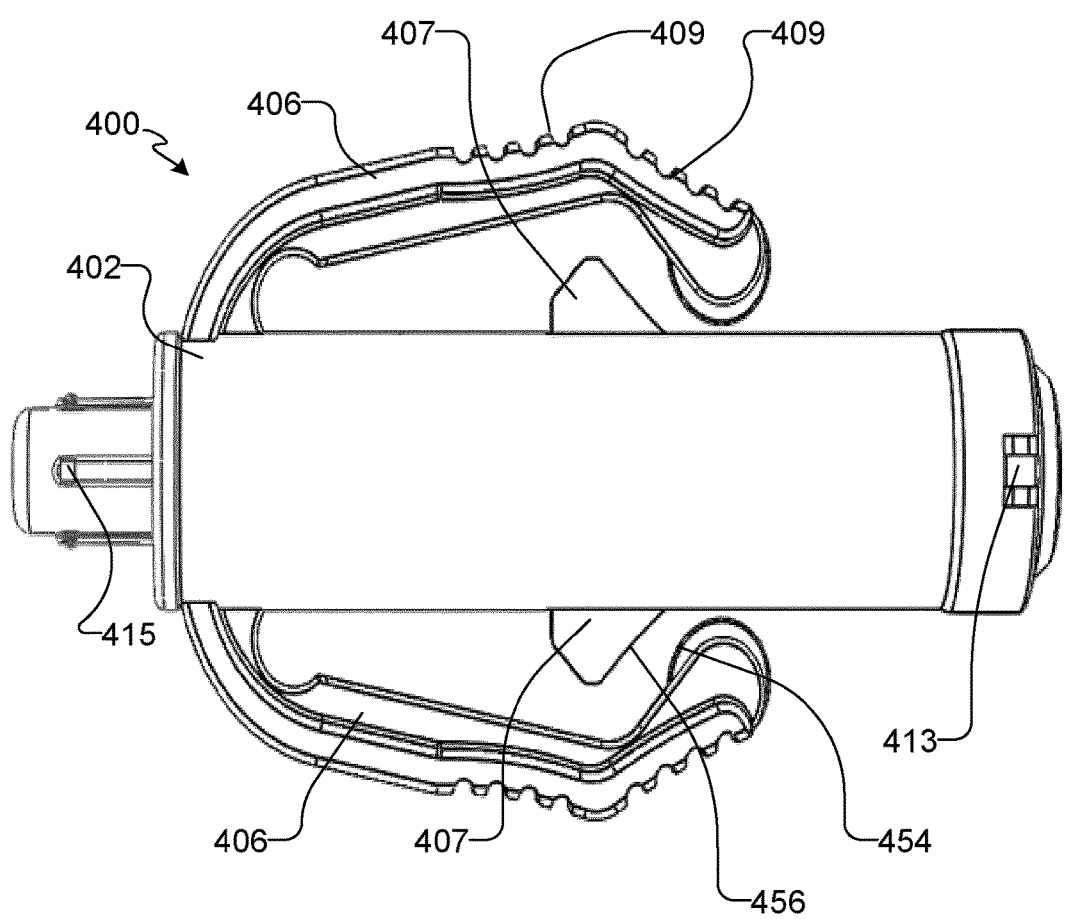
FIG. 29 is a side view showing the embodiment illustrated in FIGS. 23A-28 after the needle has been retracted.

FIG. 28 shows needle retraction assembly 472 in its retracted position within retraction lumen 444. FIG. 29 shows retractable blood collection device 400 when the needle 414 has been retracted and a user has released wings 406. Because plunger 412 has been moved distally, angled surfaces 454, 456 are no longer in contact when wings 406 are permitted to return to their initial position. Also visible in FIG. 29 are snap fit engagement projections 415 provided at the distal end of housing 402 that can be used to snap cap 401 onto the distal tip of housing 402 via corresponding depressions provided on the inner surface of cap 401.

While a number of exemplary aspects and embodiments have been discussed above, those of skill in the art will recognize certain modifications, permutations, additions and sub-combinations thereof. For example:

While propellant chamber 62 or 232 has been described as being positioned distally of spikes 68 or 278, in alternative embodiments, the relative orientations of these components could be reversed, e.g. propellant chamber 62 or 232 could be defined within spike plate ring 54 or internal or external seal 226/220, and spikes 68 or 278 could be positioned at a distal end of the path of travel of propellant chamber 62 or 232 so that movement of spike plate ring 54 or spike plate 224 a sufficient distance in the distal direction would cause propellant chamber 62 or 232 to impinge upon spikes 68 or 278, thereby rupturing seal 66 or 240.

It is therefore intended that the following appended claims and claims hereafter introduced are not to be limited by the preferred embodiments described herein, but are to be given the broadest interpretation consistent with the specification as a whole.

What is claimed is:

1. A blood collection device for use with a blood collection vial, the blood collection device comprising:
   a housing having a proximal end configured to receive the blood collection vial;
   a needle retraction assembly positioned near a distal end of the housing and moveable between an initial assembled configuration and an activated configuration in response to the application of an activation force against the blood collection vial by a user, the needle retraction assembly comprising:
   a spike plate comprising rupturing members extending distally of the needle retraction assembly; and
   a needle hub engaged with other components of the needle retraction assembly in a first position when the needle retraction assembly is in the initial assembled configuration, and moveable to a second, sealed, position within the needle retraction assembly in response to the application of the activation force to move the needle retraction assembly to the activated configuration;
   a needle supported by the needle hub, the needle having a distal end for piercing the skin of a subject and a proximal end for insertion through a cover of the blood collection vial; and
   a propellant chamber located distally of the spike plate, the propellant chamber having a seal for initially containing propellant, the seal being rupturable upon movement of the spike plate to the activated position to release the propellant;
   so that release of the propellant moves the needle retraction assembly and the needle in the proximal direction to retract the needle inside the housing.

2. A blood collection device as defined in claim 1, wherein a seal is formed between the needle hub and other components of the needle retraction assembly before the needle hub is moved to the second sealed position, optionally wherein the seal is formed after movement of the needle hub from the first position to the second position has been initiated.

3. A blood collection device as defined in claim 2, where the seal is continuously maintained until the needle hub is moved to the second position.

4. A blood collection device as defined in claim 3, wherein the needle retraction assembly comprises a retraction seal slideably engaged with an inside surface of the housing, the retraction seal supporting the spike plate within the housing.

5. A blood collection device as defined in claim 4, wherein the housing comprises one or more radially inwardly extending projections that contacts a proximal portion of the retraction seal when the needle retraction assembly is in the initial assembled position to prevent movement of the retraction assembly in the proximal direction during normal use of the blood collection device to collect blood, wherein the retraction seal is slideable over the radially inwardly extending projections to retract the needle when the propellant is released.

6. A blood collection device as defined in claim 1, wherein the needle retraction assembly comprises a retaining ring for engaging with the needle hub in the first position and in the second, sealed, position, the retaining ring optionally having a generally cylindrical shape with a retaining recess on an inside surface of the retaining ring for engaging with first and second sealing features on the needle hub.

7. A blood collection device as defined in claim 6, wherein the first and/or second sealing features on the needle hub comprise a radially outwardly extending O-ring seal; wherein optionally the first and/or second sealing features on the needle hub comprise upper and/or lower tapered seals.

8. A blood collection device as defined in claim 1, wherein the spike plate comprises an upper flange and a lower flange, and wherein the retraction seal interposes the upper flange and the lower flange; wherein optionally the upper flange and lower flange are joined by a central ring, and the retaining ring is optionally fitted inside the central ring.

9. A blood collection device as defined in claim 8, wherein the lower flange comprises an axially extending flange projecting in the distal direction for preventing formation of a seal between the lower flange and a lip of the propellant chamber when the needle retraction assembly is in the activated position; wherein optionally the lower flange sealingly engages with a central region of a distal portion of the housing inside of the propellant chamber when the needle retraction assembly is in the activated position to form a seal to prevent the flow of released propellant towards the needle hub.

10. A blood collection device as defined in claim 1, comprising a proximal needle seal for preventing flow of blood through the needle when the blood collection vial is not coupled to the blood collection device, the proximal needle seal optionally comprising a small aperture positioned over a proximal opening of the needle, so that insertion of the cover of the blood collection vial over the proximal end of the needle retracts the proximal needle seal.

11. A blood collection device as defined in claim 1, wherein the housing comprises a proximal main body and a distal needle assembly, the needle retraction assembly being supported by the distal needle assembly in its initial assembled position, wherein optionally the main body and the distal needle assembly are provided with corresponding threaded surfaces for coupling the main body to the distal needle assembly.

12. A blood collection device as defined in claim 1, comprising a stop mechanism for preventing further movement of the needle retraction assembly in a proximal direction after the needle has been retracted, wherein the stop mechanism optionally comprises a vent provided just distal of a final retracted position of the needle retraction assembly and/or a radially inwardly extending projection provided just proximal of the final retracted position of the needle retraction assembly.

13. A blood collection device comprising:
a housing;
a plunger slideably mounted within the housing, sidewalls of the plunger defining a retraction lumen within the plunger;
a needle seal frictionally engaged within the retraction lumen at a distal end of the plunger, the needle seal having a sealing engagement structure on a distal side thereof;
a needle initially secured at a distal portion of the housing;
a needle support structure frictionally engaged in the distal portion of the housing for initially securing the needle in place, a first portion of the needle support structure being moveable in a distal direction in response to application of an activation force against the plunger by a user, a second portion of the needle support structure being shaped and configured to engage with the sealing engagement structure of the needle seal upon the application of the activation force against the plunger by the user to provide a needle retraction assembly including the needle;
a propellant chamber positioned in the housing distally of the needle support structure;
rupturing spikes provided proximally of the propellant chamber and distally of the needle support structure, the rupturing spikes being moveable to rupture the propellant chamber upon the application of the activation force against the plunger by the user; and
a blood collection outlet for passing blood flowing through the needle to a blood collection reservoir;
a blood flow path being provided through the needle and past the plunger to the blood collection outlet when the blood collection device is in its initial configuration, whereby the application of the activation force against the plunger by the user moves the plunger distally within the housing to engage the needle seal with the second portion of the needle support structure to form the needle retraction assembly and causes the first portion of the needle support structure to move distally within the housing to cause the rupturing spikes to release propellant from the propellant chamber, so that the released propellant retracts the needle retraction assembly and the needle within the retraction lumen.

14. A blood collection device as defined in claim 13, wherein the housing comprises a pair of opposed wings extending radially outwardly from the housing, the wings having inwardly facing outwardly angled activation surfaces, and wherein the plunger comprises a pair of outwardly facing outwardly angled activation surfaces at a proximal end of the plunger, the outwardly angled activation surfaces on the wings being in sliding contact with the outwardly angled activation surfaces on the plunger, so that an inward activation force applied against the plunger by a user is translated into movement of the plunger in the distal direction, wherein optionally the inward activation force comprises a user squeezing the pair of opposed wings inwardly.

15. A blood collection device as defined in claim 13, wherein the needle support structure comprises a needle hub coupled to the needle, an internal seal engaged around the needle hub, and an external seal frictionally engaged in the distal portion of the housing, the needle hub and internal seal being initially retained within the external seal, the external seal being slideable in the distal direction within the distal portion of the housing in response to the application of the activation force by the user to displace the external seal from the internal seal.

16. A blood collection device as defined in claim 13, wherein the housing comprises a main body and a needle assembly, the needle assembly containing the propellant chamber and being engaged with a distal end of the housing, wherein the needle hub is restrained against movement in the distal direction in response to the application of the activation force by the user by contact with a proximal portion of the needle assembly, wherein the needle assembly optionally comprises a proximally extending neck that contacts a distal end of the needle hub.

17. A blood collection device as defined in claim 13, wherein the sealing engagement structure of the needle seal comprises a recess for receiving a proximal tip of the needle hub and a grabbing arm for engaging in snap fit with a locking edge on the proximal tip of the needle hub.

18. A blood collection device as defined in claim 17, wherein the sealing engagement structure of the needle seal comprises a central projection extending distally within the recess, and wherein the proximal tip of the needle hub comprises a correspondingly shaped aperture for receiving the central projection to form a seal between the needle seal and the needle hub.

19. A blood collection device as defined in claim 13, comprising a first circumferential seal around the plunger and in sealing engagement with an interior sidewall of the main body to prevent flow of blood past the plunger when blood is flowing through the blood flow path, and further comprising a second circumferential seal around the plunger and in sealing engagement with the interior sidewall of the main body, the first circumferential seal being moveable to an axial position distal of the blood collection outlet in response to the application of the activation force by the user, and the second circumferential seal being moveable to an axial position proximal of the blood collection outlet in response to the application of the activation force by the user, so that blood is prevented from flowing out of the blood collection outlet and past the plunger in either the proximal or distal directions.

20. A blood collection device comprising:
 a housing having a pair of opposed wings extending radially outwardly from the housing and a pair of axially extending slots formed through the housing, an inner surface of the wings comprising a first angled sliding surface;
 a plunger axially moveable within the housing, the plunger having a retraction lumen therein, and the plunger having a pair of radially outwardly extending projections, each one of the projections extending through a corresponding one of the pair of axially extending slots formed through the housing, a proximal portion of each one of the projections comprising a second angled sliding surface;
 the first and second sliding surfaces being positioned and configured so that radially inward movement of the pair of opposed wings is translated to movement of the plunger in a distal direction;
 a blood collection tubing outlet defining a fluid flow path for blood to exit through the housing;
 a needle support seal sealingly engaged with an inner surface of the housing distally of the blood collection tubing outlet;
 a needle hub initially in sealing engagement with the needle support seal and being restrained against movement in the distal direction;
 a needle coupled to the needle hub and extending from the distal end of the housing;
 a needle seal positioned at a distal portion of the retraction lumen of the plunger;
 a plunger seal positioned at a distal end of the plunger;
 a propellant chamber positioned distally of the needle support seal; and
 spikes for rupturing the propellant chamber provided distally of the needle support seal, so that movement of the needle support seal in a distal direction will cause the propellant chamber to rupture;
 a fluid path for collecting blood from a subject being defined from the needle and past the plunger to the blood collection tubing outlet when the blood collection device is in an initial unactivated configuration; and
 the plunger being moveable in a distal direction when a user applies a radially inward force to the pair of wings to:
  cause the plunger seal to seal the blood collection tubing outlet;
  cause the needle seal to sealingly engage in snap-fit engagement with the needle hub to form a needle retraction assembly comprising the needle seal, the needle hub and the needle;
  move the needle support seal in a distal direction, thereby releasing the needle hub from the needle support seal and causing the spikes to rupture the propellant chamber to release propellant to retract the needle retraction assembly.

* * * * *